(12) United States Patent
Saliman et al.

(10) Patent No.: US 11,837,344 B2
(45) Date of Patent: Dec. 5, 2023

(54) SYSTEMS AND METHODS FOR SECURELY STORING PATIENT INFORMATION AND PROVIDING ACCESS THERETO

(71) Applicant: OutcomeMD, Inc., Los Angeles, CA (US)

(72) Inventors: Justin Saliman, Los Angeles, CA (US); Jason Hurst, Vancouver, WA (US); Karthik Karunanithi, Los Angeles, CA (US); Ryan Saliman, Los Angeles, CA (US); Douglas Grim, Portland, OR (US); Darin Feinstein, Los Angeles, CA (US)

(73) Assignee: OutcomeMD, INC., Los Angeles, CA (US)

( * ) Notice: Subject to any disclaimer, the term of this patent is extended or adjusted under 35 U.S.C. 154(b) by 300 days.

(21) Appl. No.: 16/457,744

(22) Filed: Jun. 28, 2019

(65) Prior Publication Data

US 2020/0005912 A1 Jan. 2, 2020

Related U.S. Application Data

(60) Provisional application No. 62/692,284, filed on Jun. 29, 2018.

(51) Int. Cl.
| | |
|---|---|
| *G16H 10/20* | (2018.01) |
| *G16H 10/60* | (2018.01) |
| *G06F 21/31* | (2013.01) |
| *G06F 21/62* | (2013.01) |

(Continued)

(52) U.S. Cl.
CPC ............. *G16H 10/60* (2018.01); *G06F 21/31* (2013.01); *G06F 21/6245* (2013.01); *G16H 10/20* (2018.01); *H04L 9/50* (2022.05); *H04W 12/02* (2013.01)

(58) Field of Classification Search
CPC ........................ G06Q 50/22–24; G16H 10/60
See application file for complete search history.

(56) References Cited

U.S. PATENT DOCUMENTS

| | | |
|---|---|---|
| 8,615,532 B2 | 12/2013 | Bessette |
| 9,635,000 B1 | 4/2017 | Muftic |
| 9,722,790 B2 | 8/2017 | Ebrahimi |

(Continued)

FOREIGN PATENT DOCUMENTS

| | | | | |
|---|---|---|---|---|
| CN | 106934243 | * | 7/2017 | |
| WO | WO-2015191760 A2 | * | 12/2015 | ........... C07K 16/241 |

OTHER PUBLICATIONS

"Blockchain Technology for Healthcare: Facilitating the Transition to Patient-Driven Interoperability"; Gordon et al.; Computational and Structural Biotechnology Journal 16 (2018) 224-230; Jun. 3, 2018. (Year: 2018).*

(Continued)

*Primary Examiner* — John A Pauls
(74) *Attorney, Agent, or Firm* — RESONANCE IP LAW, PC

(57) ABSTRACT

Upon receipt and verification of a patient's key, a medical questionnaire may be provided to a patient via an electronic device (e.g., computer, mobile phone, etc.). A set of responses to the medical questionnaire may be received from the patient and packaged for storage on a blockchain. The packaged set of responses may then be broadcast to the blockchain.

18 Claims, 25 Drawing Sheets

(51) Int. Cl.
*H04W 12/02* (2009.01)
*H04L 9/00* (2022.01)

(56) References Cited

U.S. PATENT DOCUMENTS

| | | | |
|---|---|---|---|
| 9,836,908 B2 | 12/2017 | Spanos et al. | |
| 9,849,364 B2 | 12/2017 | Tran et al. | |
| 10,878,512 B1* | 12/2020 | Al-Zoubi | H04L 9/3239 |
| 2006/0074719 A1* | 4/2006 | Horner | G16H 10/20 |
| | | | 705/3 |
| 2008/0167932 A1* | 7/2008 | Capozzi | G06Q 30/00 |
| | | | 705/7.19 |
| 2009/0125331 A1* | 5/2009 | Pamsgaard | G16H 40/63 |
| | | | 705/3 |
| 2015/0012295 A1* | 1/2015 | Mahoney | G16H 10/20 |
| | | | 705/3 |
| 2015/0112722 A1* | 4/2015 | Dees | A61B 5/0022 |
| | | | 705/3 |
| 2015/0332283 A1 | 11/2015 | Witchey | |
| 2017/0091397 A1 | 3/2017 | Shah | |
| 2017/0206324 A1* | 7/2017 | Reicher | G06Q 50/22 |
| 2017/0300627 A1* | 10/2017 | Giordano | G06F 21/6245 |
| 2017/0300872 A1* | 10/2017 | Brown | G06Q 20/3827 |
| 2019/0019180 A1* | 1/2019 | Coburn | H04L 9/0637 |

OTHER PUBLICATIONS

"An Introduction to Smart Contracts and Their Potential and Inherent Limitations"; Levi et al.; May 26, 2018. (Year: 2018).*

Ekblaw, Ariel et al., "A Case Study for Blockchain in Healthcare: "MedRec" prototype for electronic health records and medical research data," White Paper, Aug. 2016, 13 pages.

Ekblaw, Ariel et al., "MedRec: Medical Data Management on the Blockchain," Apr. 11, 2016, 5 pages, https://viral.media.mit.edu/pub/medrec.

MedicalChain Whitepaper 2.1, 2018, 42 pages.

Wagner, Jayce, "The tech behind cryptocurrency could save lives by fixing medical records", Apr. 16, 2018, 20 pages, https://www.digitaltrends.com/computing/how-the-blockchain-could-change-healthcare-and-save-lives/.

* cited by examiner

501

502

800

701

702

703

704

705

706

707

708

709

SYSTEMS AND METHODS FOR SECURELY STORING PATIENT INFORMATION AND PROVIDING ACCESS THERETO

RELATED APPLICATION

This application is a NON-PROVISIONAL of, and claims priority to, U.S. Provisional Patent Application No. 62/692,284 filed on 29 Jun. 2018 and entitled "SYSTEMS AND METHODS FOR SECURELY STORING PATIENT INFORMATION AND PROVIDING ACCESS THERETO," which is hereby incorporated, in its entirety, herein.

FIELD OF THE INVENTION

The present invention relates to medical information technology. More specifically, the present invention relates to systems and methods for securely storing patient information and providing access thereto.

BACKGROUND

Communication of personally identifiable information and personal medical data is fraught with security concerns. Traditionally used systems do not adequately protect this sensitive information from security threats. Additionally, traditional systems do not provide verifiable and trusted sources of medical data.

SUMMARY

Systems and methods for securely storing patient information and providing access thereto are herein provided. The patient data may be stored on a distributed ledger and/or a blockchain. In some embodiments, a patient's key (e.g., encryption key or public key) may be received by, for example, a processor, computer, or blockchain administrator from, for example, a patient's electronic device (e.g., smart phone or computer). The key may be verified and, responsively to the verification, an outcome measurement device (OMD) (e.g., a medical questionnaire) may be provided to a patient so that, for example, it may be displayed on his or her personal electronic device.

A set of responses to the OMD and/or medical questionnaire may be received from the patient and packaged for storage on a blockchain. Packaging the set of responses may include formatting the set of responses for storage on the blockchain. The packaged set of responses may then be broadcast or otherwise communicated to the blockchain. The blockchain may be public, private, or some combination thereof. In some embodiments, the set of responses may be associated with the patient's electronic medical record prior to, or following, the packaging and/or broadcasting.

In some embodiments, the OMD medical questionnaire may be associated with a scoring procedure for scoring the set of responses and the scoring procedure may be applied to the set of responses to determine a wellness score for the patient. The wellness score may then be packaged for storage on the blockchain and broadcast or otherwise communicated to the blockchain.

In some cases, a first medical questionnaire may be provided to the patient and a subsequent second medical questionnaire may be provided to the patient. The second medical questionnaire may be the same as the first medical questionnaire. Upon facilitating provision of the second medical questionnaire to the patient, a second set of responses may be received from the patient. The second set of responses may be packaged for storage on the blockchain and the packaged second set of responses may be broadcast to the blockchain. In some embodiments, the blockchain may be queried for the first and second set of responses, which may be received responsively to the query. An improvement score for the patient may be then be determined by comparing the first and second set of responses. The improvement score may indicate a result of the comparison on, for example, a question-by-question and/or overall basis.

Additionally, or alternatively, in embodiments where first and second wellness scores for the patient are determined using the respective first and second set of responses, the blockchain may be queryied for the first and second wellness scores, the first and second wellness scores may be compared and an improvement score may be determined based on the comparison. The improvement score may then be packaged for storage on the blockchain and broadcast to the blockchain.

Additionally, or alternatively, in some instances, the set of responses may be digitally signed. This may occur prior to packaging the set of responses and if so, the digitally signed and packaged set of responses may be broadcast to the blockchain.

Additionally, or alternatively, the medical questionnaire may be associated with a smart contract that includes smart contract a requirement and a condition. Exemplary requirements include, but are not limited to, answering questions, performing tasks, completing the medical questionnaire and/or OMD, and/or completing a percentage of the total questions provided by the medical questionnaire, etc. Exemplary tasks include, but are not limited to, making an appointment to see a medical professional or attending an appointment to see a medical professional, complying with a treatment regimen, etc. When it is determined that the requirement is met, then the condition may be fulfilled. Exemplary conditions include, but are not limited to, monetary rewards, awards of points, access to privileges, etc. In some instances, an indication of fulfillment of the condition may be packaged for storage on the blockchain. This packaging may include association of patient information and/or a patient identifier. Then, the packaged indication may be broadcast to the blockchain. In some embodiments, the patient may be provided with an indication that the condition has been fulfilled in the form of, for example, a message communicated to his or her electronic device.

Additionally, or alternatively, patient, in some instances, may be associated with a patient identifier and the packaging of the set of responses for storage on the blockchain includes associating the patient identifier with the set of responses. Additionally, or alternatively, the packaging of the set of responses for storage on the blockchain may include associating the patient key with the set of responses.

BRIEF DESCRIPTION OF THE DRAWINGS

The present invention is illustrated by way of example, and not limitation, in the figures of the accompanying drawings in which.

Figure 1A:
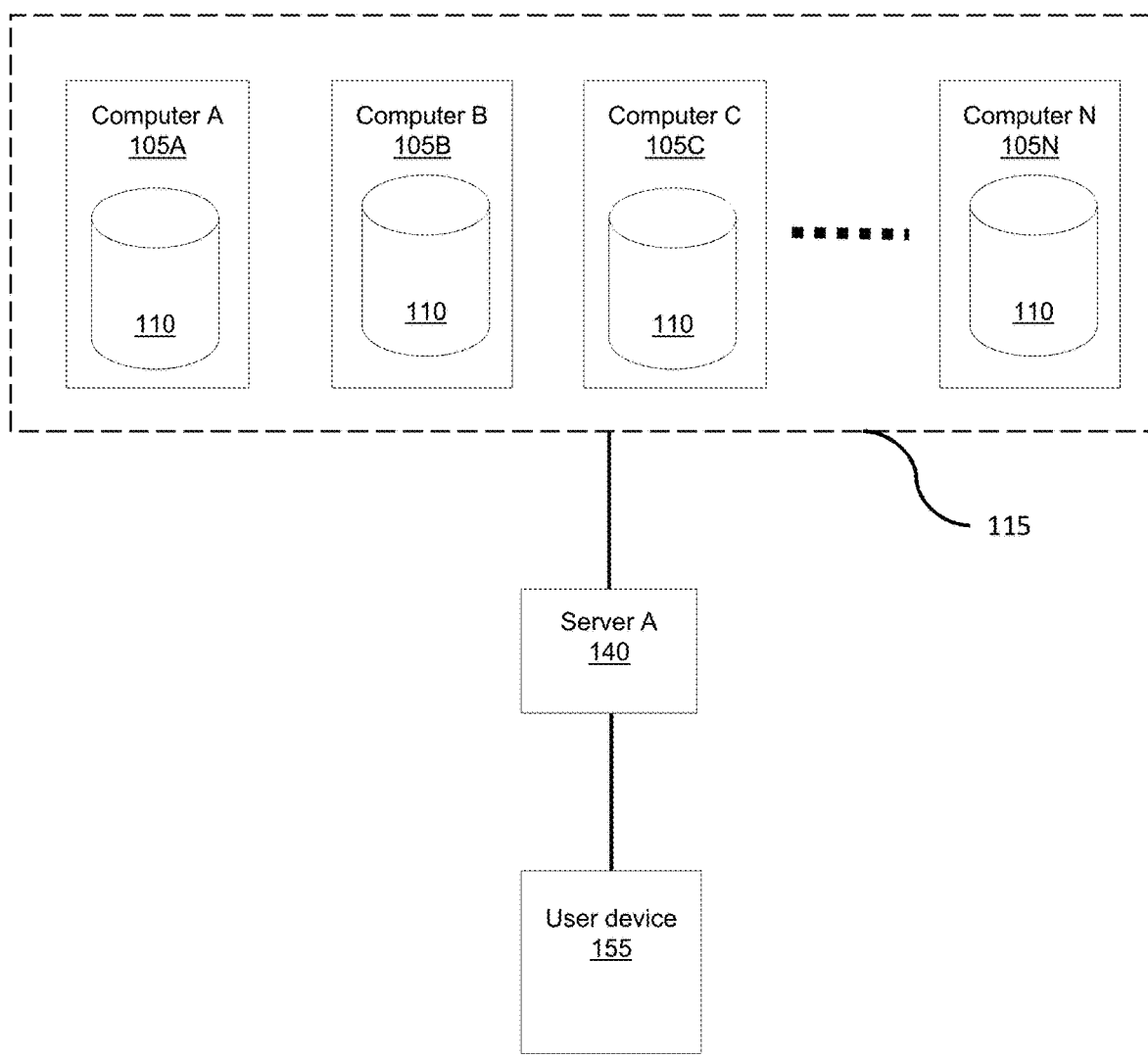
FIG. 1A provides a block diagram of an exemplary system of an array of a plurality of computers 105A-105N on which a distributed ledger and/or blockchain 110 may be stored, consistent with some embodiments of the present invention.

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

WRITTEN DESCRIPTION

Patients, or other individuals, may wish to store and/or communicate information regarding their heath, medical condition, and/or medical history via a patient account. The patient account may include medical information entered by the patient him or herself, a care giver for the patient (e.g., nurse or family member), treatment facility (e.g., hospital or clinic), and/or a medical treatment provider, which may be referred to herein as a "provider." Exemplary providers include, but are not limited to, doctors, nurses, case managers, technicians, and medical school residents. In some instances, the patient account may include a particular patient's electronic medical records (EMR), which may also be referred to as an electronic health record (EHR). As used herein "patient information" may include, but is not limited to, patient identification information, patient medical history, patient notes, and so on.

The patient account is a place where a patient and his or her medical professionals may enter data regarding the patient and his or her health. Information stored in and/or associated with a patient account may be accessed and, in some instances, may be added to and/or modified by the patient or care giver via a patient portal linked to the patient account. In many instances, the patient portal is provided to the patient/caregiver via one or more GUIs displayed on user device (e.g., smart phone or computer). A provider may view information regarding the patient via a provider portal via one or more GUIs displayed on user device (e.g., smart phone, tablet, or computer).

Information provided by the patient portal and the provider portal may be the same and/or different. In some embodiments, information provided via the provider portal may be presented in medical terminology/nomenclature and information provided via the patient portal may be provided in terminology more easily understood by those not in the medical profession. Privileges to add and/or modify information associated with a patient account may be different for patients/care givers and providers. For example, a patient may not be able to modify, or add to, information entered by a provider regarding an encounter (e.g., office visit), prescription of a medication or treatment, or an interpretation of lab test results.

In some embodiments, a provider portal may include information regarding a patient encounter or other provider interaction with a patient that may be presented to a provider via a medical note interface. The medical note interface may be a vehicle to, for example, document the patient encounter, add information to the patient's EMR, and, in some instances, may facilitate the billing of the patient encounter or otherwise provide compliance with one or more accounting or other rules for classifying the patient encounter.

In some embodiments, a patient may receive a request for information regarding his or her health, treatment recovery, treatment compliance, and/or general health. In some embodiments, this request may be received by the patient as, for example, a request to complete an outcome measurement device (OMD), which may be, for example, a questionnaire and/or a patient reported outcome (PRO) instrument and/or a request to complete a test and/or provide a measurement of the patient's health (e.g., blood sugar, vital signs, blood coagulation factor, lung capacity, etc.). When the requested information is received from the patient, a wellness score may be determined therefrom by analyzing the received responses according to one or more scoring metrics associated with, for example, the OMD provided to the patient, baseline patient data, a test performed, demographic data associated with the patient (e.g., age, gender, body mass, etc.). In some instances, received information may be used to determine an improvement score for the patient. An improvement score may be determined via, for example, comparing a current wellness score with a previously determined wellness score for the patient and/or a particular category of information for which the patient has provided information. Additionally, or alternatively, a compliance score that provides an indication of the patient's compliance with a medical treatment may also be determined using the received information. Further information regarding wellness scores, improvement scores, compliance scores, and the determination thereof as well as systems used to make determinations thereof is provided in U.S. patent application Ser. Nos. 15/427,962 and 15/673,236.

FIG. 1A provides a block diagram of an exemplary system 100 of an array 115 of a plurality of computers 105A-105N on which a distributed ledger and/or blockchain 110 may be stored. A user may add information to and/or extract information from distributed ledger and/or blockchain 110 via interaction with, for example, a user device 115 that is in communication with a server A 140. Server A 140 may be any computer system that facilitates communication between user device 155 and the computers of array 115 and/or distributed ledger and/or blockchain 110. In some embodiments, server A 140 may act as a gatekeeper and may execute various security protocols (e.g., verification of passwords, digital signatures, permissions, or other credentials) that enable access to array 115, a computer 105A-105N, distributed ledger and/or blockchain 110, and/or information stored thereon. In some instances, server A 140 may establish a DNS-like mapping between a commonly used form of ID (name, patient ID, user account password, etc.) and on-blockchain addresses. Server A 140 may also register new users, patients, etc. and/or change the mapping of existing users, patients, etc. according to, for example, patient or treatment provider needs. Exemplary user devices 115 include, but are not limited to, computers, mobile phones, tablet computers, and the like.

At times, array 115 may be a large network of tens, hundreds, thousands (or more) computers. In some instances, array 115 may include a permissionless blockchain network (e.g., Bitcoin and Ethereum) that is used by a plurality of enterprises and individuals to store information. Maintaining privacy while using this open availability may be facilitated via one or more security protocols (e.g., public/private key encryption, passwords, etc.). In some instances, array 115 and/or distributed ledger and/or blockchain 110 may be a private system (sometimes referred to herein as a private blockchain) operated, managed, and/or maintained by, for example, a single entity or enterprise that stores a private, or permissioned, distributed ledger and/or blockchain 110. When distributed ledger and/or blockchain 110 is specific to an enterprise, accessing the distributed ledger and/or blockchain 110 may require use of security protocols specific to the distributed ledger and/or blockchain 110 and/or enterprise operating and/or managing the distributed ledger and/or blockchain 110 that may be managed and/or administrated by server A 140. Even when array 115 is privately operated and/or distributed ledger and/or blockchain 110 is private, interaction between user device 155 and array 115, server A 140, computers 105A-105N and/or distributed ledger and/or blockchain 110 may be user device 155 agnostic in that no specific requirements for the user device 155 (other than ability to communicate with server A 140) may be required. Thus, information may be able to pass between user device 155, array 115, server A 140, computers 105A-105N and/or distributed ledger and/or blockchain 110 regardless of software or hardware constraints.

Figure 1B:
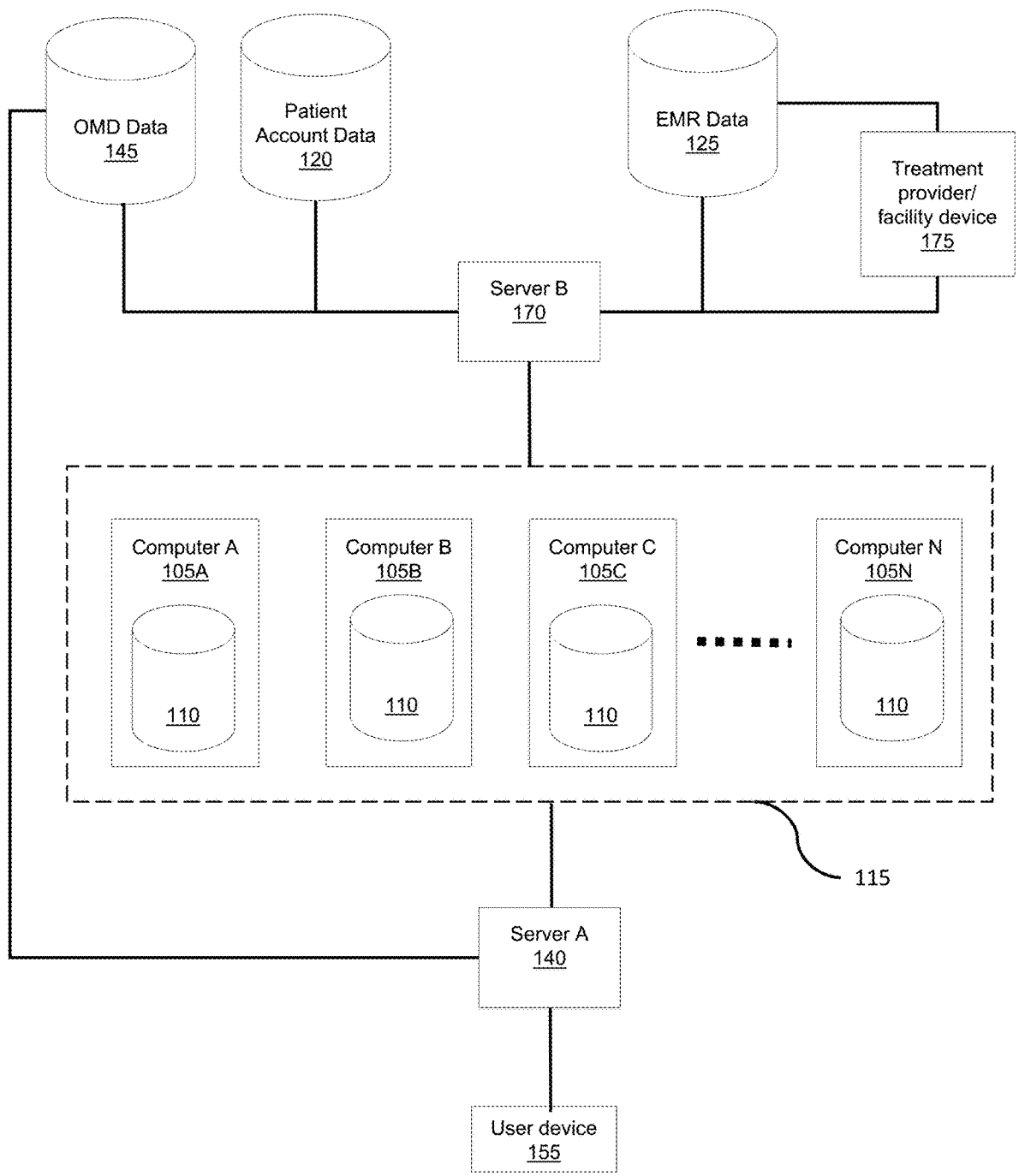
FIG. 1B provides a block diagram of another exemplary system, consistent with some embodiments of the present invention.

FIG. 1B provides a block diagram of another exemplary system 101 that includes all the components of system 100, a server B 170, a treatment provider/facility device 175, a patient account database 120, an optional EMR database 125, and an optional OMD database 145. Patient account database 120 stores information associated with a plurality of patient accounts including, but not limited to, patient identifying information, OMD responses, determined outcome scores, determined improvement scores, treatments, patient notes. EMR database 125 stores electronic medical record information for one or more patients, some of whom may have a patient account and information about that corresponding patient account may be stored in patient account database 120. In some embodiments of system 101, EMR database 125 may be optional. In these instances, electronic medical record data may be associated with corresponding patient accounts stored in patient account database 120. In some embodiments, patient information (including EMR information) may be stored in one or more of computers A-N 105A-105N. OMD database stores various OMDs and, in some instances, may store criterial for the assignment of an OMD to a particular patient and/or identifiers for patients to whom the OMD should be delivered.

Treatment provider/facility device 175 may be a computer, or the like, that facilitates communication between a treatment provider (e.g., doctor, nurse, etc.) and/or treatment facility (e.g., clinic, hospital, assisted care facility, etc.) and server B 170. At times, treatment provider/facility Device 175 may populate patient account database 120 and/or EMR database 125 with patient information. Server B 170 may be any computer device configured to facilitate communication between array 115, computers A-N 105A-105N, and/or distributed ledger and/or blockchain 110. Often times, server 170 will manage data storage within patient account database 120 and/or EMR database and access there to.

In some embodiments, patient information may be stored in patient account database 120 and/or EMR database 125 and a link to patient information may be stored in distributed ledger and/or blockchain 110. In these embodiments, a request for patient information may be communicated to server A 140 by user device 155 or communicated to server B by treatment providers/facility device 175. After verifying that the respective user of user device 155 and/or treatment provider/facility device 175 it is authorized to access the requested patient information, server A 140 or server B 170 may access distributed ledger and/or blockchain 110 to retrieve the requested patient information. If the requested patient information is stored on distributed ledger and/or blockchain 110, the request of patient information may be extracted from distributed ledger and/or blockchain 110 and provided to user device 155 or treatment provider/facility device 175.

In some embodiments, distributed ledger and/or blockchain 110 may store a link to the requested patient information and not the patient information itself. When a request for patient information is received by server A 140 or server B 170, server A 140 or server B 170 may query distributed ledger and/or blockchain 110 for the information and/or a link to the patient information. When distributed ledger and/or blockchain 110 includes a link to the patient information, this link may be provided to and/or extracted by server A 140 or server B 170. Server A 140 or server B 170 may then provide the link to the requesting device (i.e., user device 155 of treatment provider/facility device 175) and/or may use the link to retrieve the information associated therewith from the patient account database 120 or patient EMR database 125 and may then provide the retrieved information to the requesting device. Storing a link to patient information (as opposed to the patient information itself) on distributed ledger and/or blockchain 110 may serve to, for example, preserve storage space on the distributed ledger and/or blockchain and/or increase privacy for the patient information. In some cases, security of the patient information may be augmented via one or more security protocols associated with the link and/or activation thereof.

Figure 2:
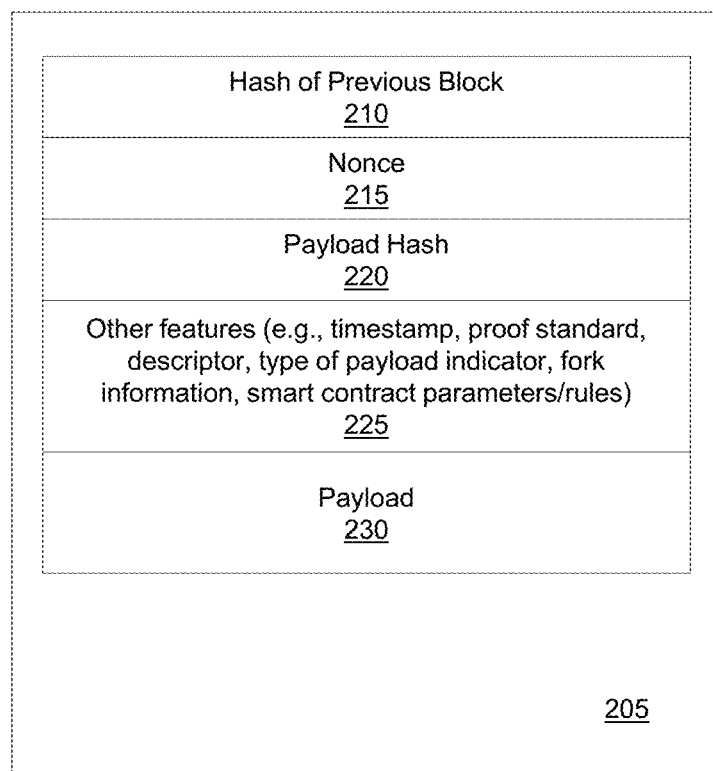
FIG. 2 provides a diagram of an exemplary data block that may be stored in the distributed ledger and/or on the blockchain, consistent with some embodiments of the present invention.

FIG. 2 provides a diagram of an exemplary data block 205 that may be stored in a distributed ledger and/or a blockchain such as distributed ledger and/or blockchain 110. Data block 205 may be structured to be compliant with one or more requirements of storage on a blockchain stored on and/or maintained by distributed ledger and/or blockchain 110. Data block 205 includes a hash of a data block previously stored on the blockchain 210 stored on and/or maintained by distributed ledger and/or blockchain 110, a nonce 215, a payload hash 220, one or more other features 225 including, but not limited to, a timestamp, a proof standard, a descriptor, a digital signature, a type of payload indicator, fork information, and/or smart contract parameters or rules, and a payload 230. Exemplary payloads 230 include, but are not limited to, medical questionnaires, answers to medical questionnaires, wellness scores, improvement scores, EMR information, treatment compliance information, personally identifiable information, patient account information, treatment information, projected wellness scores, projected improvement scores, recommendations, medical treatment provider notes, etc. and a link or other pointer to same. Payload 230 may include information communicated by a patient, a provider, a treatment provider, and/or a third party. In some embodiments, payload 230 may include information from multiple sources. In some instances, payload 230 may be a link (e.g., a hyperlink), pointer, or other indicator that may direct someone who selects or opens the link/pointer/indicator to a file or other information about a patient. This arrangement may serve to further protect a patient's privacy because his or her information is not being stored on a publicly available/accessible blockchain. Instead, only a link to the information is stored on the publically available blockchain. Thus, a user may indirectly access patient account information without it being directly stored on a publically accessible blockchain. One or more security protocols (e.g., passwords, SIM card number validation, source of the request verification, etc.) may be in place to protect the security of the patient information that is accessed via activation of the link/pointer/indicator.

Figure 3:
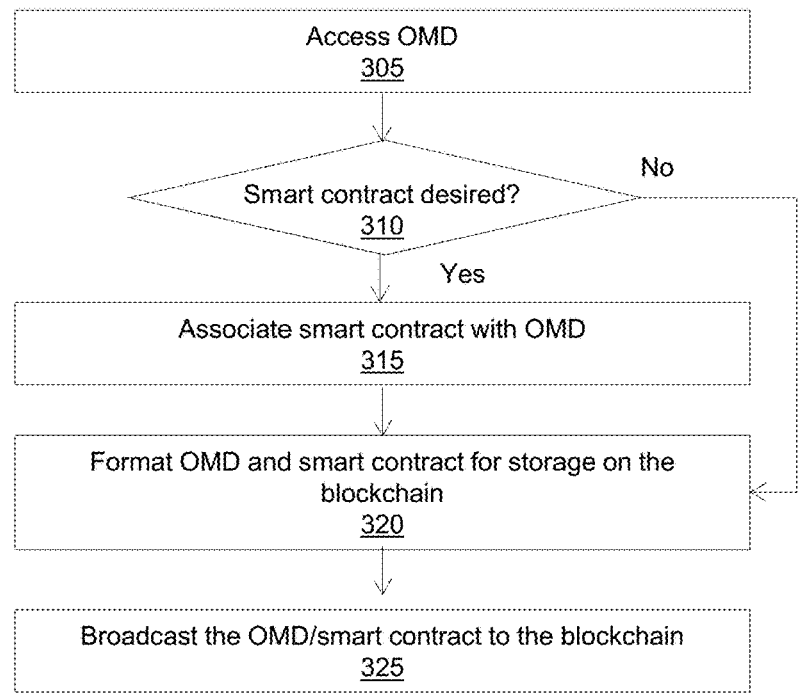
FIG. 3 provides a flowchart of an exemplary process for readying an OMD for storage on a blockchain and/or a distributed ledger, consistent with some embodiments of the present invention.

FIG. 3 provides a flowchart of an exemplary process 300 for readying an OMD for storage on a blockchain and/or a distributed ledger like distributed ledger and/or blockchain 110. Process 300 may be executed by, for example, system 100, system 101, or any component thereof.

Initially, an OMD may be accessed, retrieved, or otherwise opened (step 305). In one example, the OMD may be retrieved from OMD database 145 responsively to a request received from a user device like user device 155 or a treatment provider/facility device like treatment provider/facility device 175 by way of communication via server A 140 or server B 170, respectively. In another example, an OMD may be stored on a user device like user device 155, a treatment provider/facility device like treatment provider/facility device 175, and/or a server like server A 140 or server B 170.

In step 310, it may be determined whether association of the OMD with a smart contract is desired. If not, process 300 may proceed to step 320. When inclusion of a smart contract with the OMD is desired, a smart contract may be added to (or otherwise associated with) the OMD (step 315). A smart contract may include one or more auto-executing routines that are initiated upon satisfaction of one or more requirements and/or parameters. Exemplary requirements/parameters include, but are not limited to, viewership rights, editing rights, expiration rules, verification rules, rules regarding completion of the OMD, rules regarding incentives that may be provided to a patient or completing an OMD, rules regarding follow up processes that may be executed upon satisfaction of the smart contract or a portion thereof, and custom procedures.

In some instances, a smart contract may be a computer protocol, or code, that represents a contract that may be digitally partially, or wholly, self-executing and/or self-enforcing upon performance of one or more conditions or transactions (e.g., performance of one or more steps of process 300) without the need for a third party. A smart contract may use or incorporate a smart contract computer language, a Byzantine fault tolerant algorithm, and/or Turning-complete smart contract language as may be compatible with a blockchain and/or distributed ledger like distributed ledger and/or blockchain 110. At times, a smart contract may be facilitated by a smart contract system may be added to and/or on top of, the blockchain.

In some embodiments, exemplary smart contracts may relate to benefits or other incentives provided to a patient in response to a patient's provision of information requested by an OMD, accessing his or her patient account, and/or providing information to his or her patient account. Additionally, or alternatively, a smart contract may be responsive to the content of the data/information provided by the patient. For example, if the patient enters information that indicates he or she has lost weight, complied with a treatment regimen, or exercised, then a benefit proscribed by the smart contract may be provided to the patient. Exemplary benefits may include financial rewards, discounts, messages, awards, and so on.

Additionally, or alternatively, smart contracts may relate to communication between, for example, the patient and his or her treatment provider, treatment facility, and/or health insurance company. For example, when a patient partially, or wholly, completes an OMD, a smart contract associated with the OMD may execute to send a message to, for example, the patient's treatment provider, treatment facility, healthcare management company, and/or health insurance company indicating same. In some instances, this message may include further information regarding, for example, the OMD, a diagnosis for the patient, a treatment for the patient, a wellness score for the patient, an improvement score for the patient and so on. In some embodiments, the message may be directed to a healthcare management company or third party (e.g., an academic institution) for the exemplary purpose of gathering medical data and treatment outcome data for the study of, for example, medical conditions and/or patient behavior.

In some instances, execution of the smart contract may grant access to information and/or provide a privilege for the patient and/or treatment provider, treatment facility, and/or health insurance company. For example, a patient may be provided with the privilege of scheduling a treatment procedure following completion of the requirements of a smart contract included in/associated with an OMD.

Then, the OMD and smart contract may be formatted for storage on a blockchain and/or distributed ledger (e.g., distributed ledger and/or blockchain 110) (step 320). Then, the OMD and smart contract (when appropriate) may be broadcast to the distributed ledger and/or blockchain (step 325).

Figure 4:
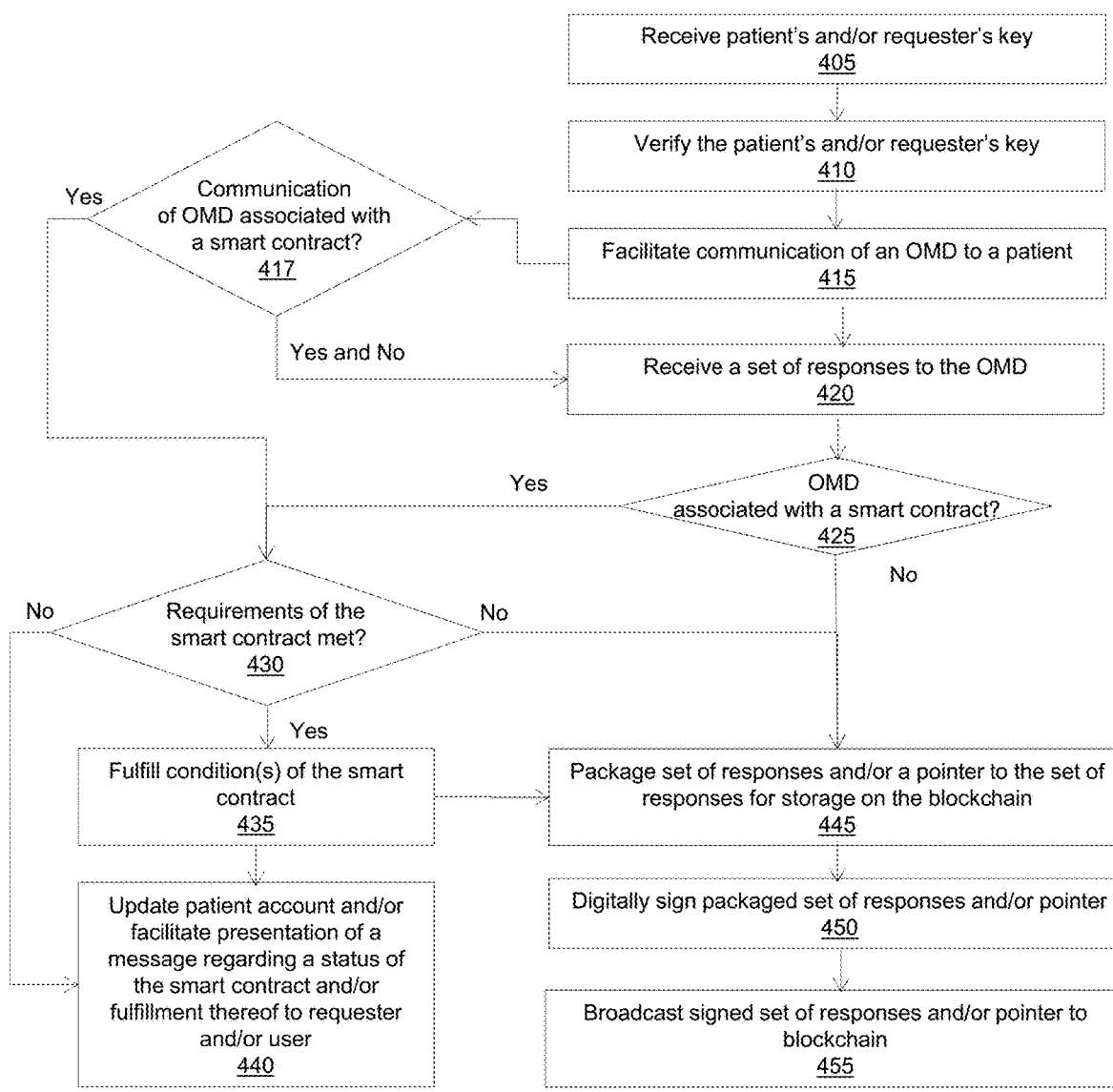
FIG. 4 provides a flowchart of an exemplary process for receiving a set of responses to an outcome measurement device from a patient and broadcasting those responses to a distributed ledger and/or blockchain, consistent with some embodiments of the present invention.

FIG. 4 provides a flowchart of an exemplary process 400 for receiving a set of responses to an OMD from a patient and broadcasting those responses to a distributed ledger and/or a blockchain like distributed ledger and/or blockchain 110. Process 400 may be executed by, for example, system 100, system 101, or any component thereof.

Initially, in step 405, a patient's and/or requester's key may be received by, for example, a computer like computer A 105A-computer N 105N. As used herein, the key may be, for example, a user name, a password, biometric information, a cryptographic key or some combination thereof. Additionally, or alternatively, a key may be a cryptographic key (e.g., a private/public key) stored on the patient's device that is communicated to, for example, a server (e.g., server A 140 and/or server B 175) providing the OMD that is accessed and/or activated when the patient signs into his or her patient account (via, for example, entry of a password). In some instances, step 405 may also include a request to access a patient account.

The patient's and/or requester's key may then be verified (step 410). Typically, this step is performed by the computer facilitating execution of step 405 but, this need not be the case. If the patient's and/or requester's key is not verified, execution of process 400 may end.

Then, in step 415, communication of an OMD to a patient may be facilitated. In some instances, the OMD may be stored on one or more of computers A-N 105A-105N, distributed ledger and/or blockchain 110, or OMD database 145. Execution of step 415 may be responsive to a request for an OMD received from a patient. In some instances, the request will include information identifying the OMD (e.g., a name of the OMD, a medical condition associated with the OMD, a demographic of a patient who is to receive the OMD, etc.). This request may be received from, for example, a patient device like patient device 155 when, for example, a patient logs onto his or her patient account. Additionally, or alternatively, the received request may be responsive to an instruction communicated to, or otherwise associated with, the patient's account indicating that a patient should receive an OMD. This instruction may be received from, for example, a provider or medical facility responsively to, for example, scheduling of the patient for a treatment, an answer a patient has provided to a previously answered OMD, and/or a patient complaint. The OMD may be communicated to, for example, a patient device, like patient device 155 and/or a computer operated by, for example, a treatment provider and communication of the OMD may be facilitated by, for example, a computer such as computer A 105A-computer N 105N.

In step 417, it may be determined whether communication of the OMD is associated with a smart contract and, if so, it may be determined whether such communication meets the requirements of the smart contract (step 430). The smart contract may be directed to a doctor or other medical provider wherein an incentive is provided to send OMDs to patients to incentivize, or otherwise reward, them to follow up on their patients.

Figure 5A:
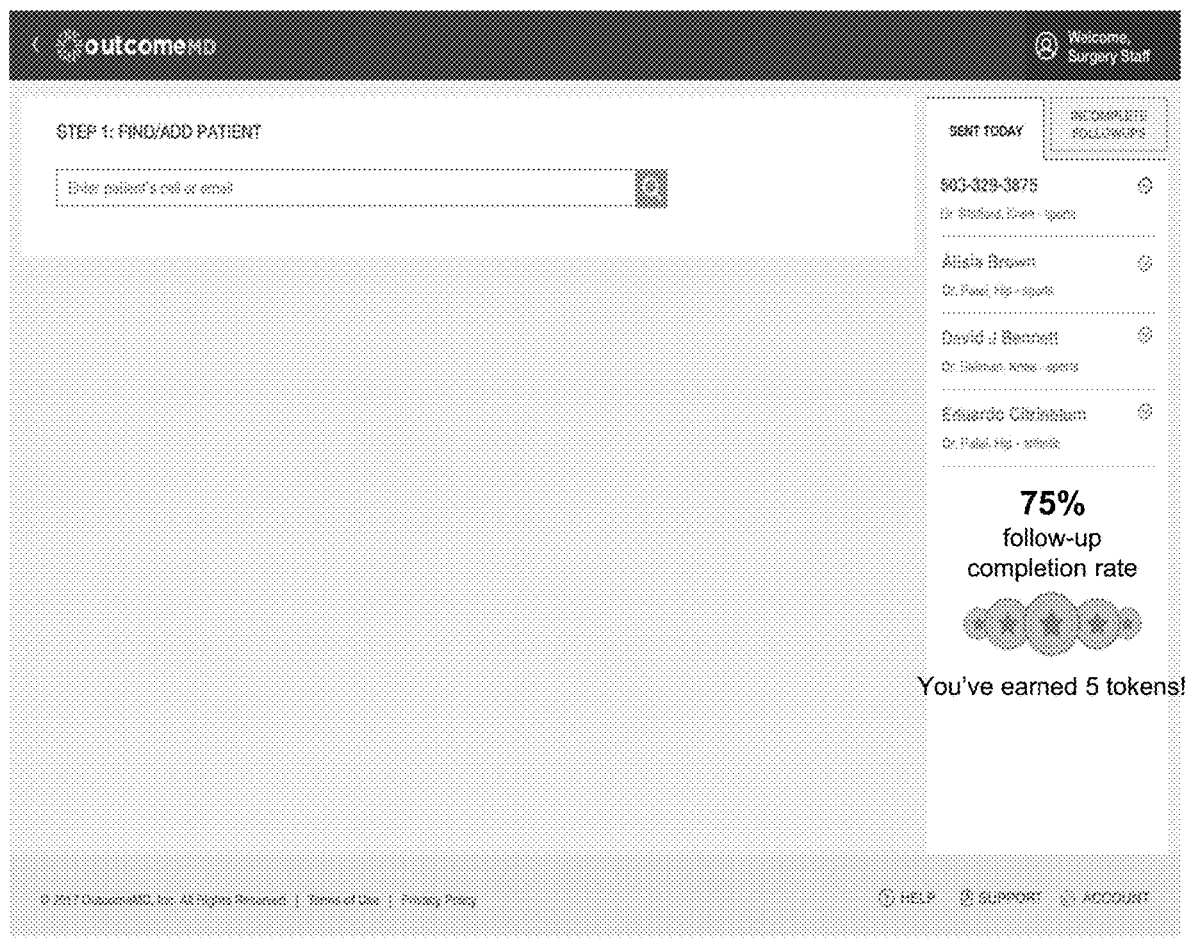
FIGS. 5A and 5B provide screen shots of exemplary interfaces, consistent with some embodiments of the present invention.
Figure 5B:
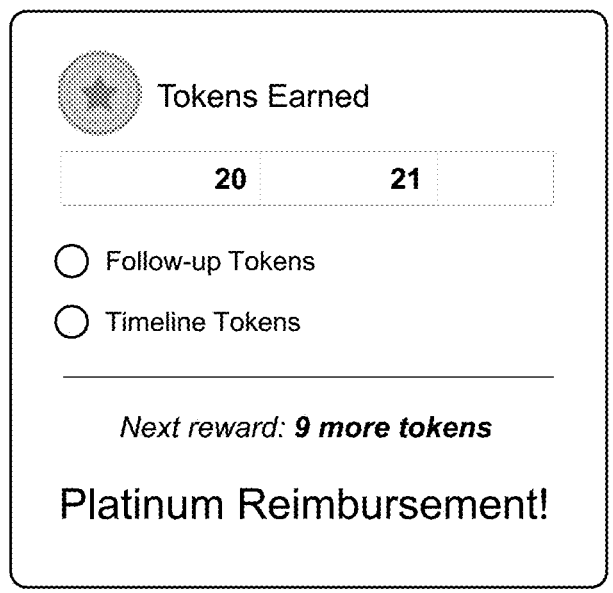

FIGS. 5A and 5B provide screen shots of exemplary interfaces 501 and 502, respectively, that may be generated via execution of process 400 or portions thereof, particularly step 440. Interface 501 provides a list of patients to whom OMDs have been sent and a message indicating that the status of a smart contract (i.e., "75% follow-up completion rate. You've earned 5 tokens") that may be displayed to a provider. Interface 502 provides a tally of incentives (i.e. tokens) earned by the provider via fulfilment of one or more smart contracts and what the incentives may be converted to (i.e., a gift card to a retail establishment.

At times, communication of an OMD to a patient may be initiated/facilitated by an assistant to a provider (e.g., medical administrator, nurse, etc.) and he or she may also receive incentives or benefits for initiating communication of an OMD to the patient. Interface 501 provides an exemplary portal by which a treatment provider may access information about one or more patients by, for example, entering the patient's name or other identifier into the text entry box. Interface 501 also provides a list of patients with whom the provider interacted. This list indicates which of these patients have been sent an OMD in green with an icon including a check mark positioned within a circle next to the patient name and which of these patients have not been sent an OMD in red with a dash positioned within a circle next to the patient name. The bottom of the list provides an indication of the percentage of patients that have been sent an OMD (indicated on interface 501 with the message "75% follow-up completion rate") along with a message indicating an incentive that has been earned by sending out the OMDs, in this case 5 tokens.

Interface 502 of FIG. 5B provides a tally of the tokens earned by the provider for sending out OMDs to follow up after office visits (shown as follow-up tokens) and sending out OMDs according to a timeline or schedule (shown as timeline tokens). Interface 502 also includes a message indicating how many more incentives must be earned to reach the next reward (in this case 9 more tokens) along with a statement regarding an incentive (in this case, platinum reimbursement). Providers may earn tokens by, for example, using a provider portal, updating information stored via the provider portal, updating patient accounts, interacting with patients, initiating communication of an OMD to a patient, review of OMD responses, review or editing of a patient note interface, rates of patient participation with his or her respective patient account, etc.

Figure 6:
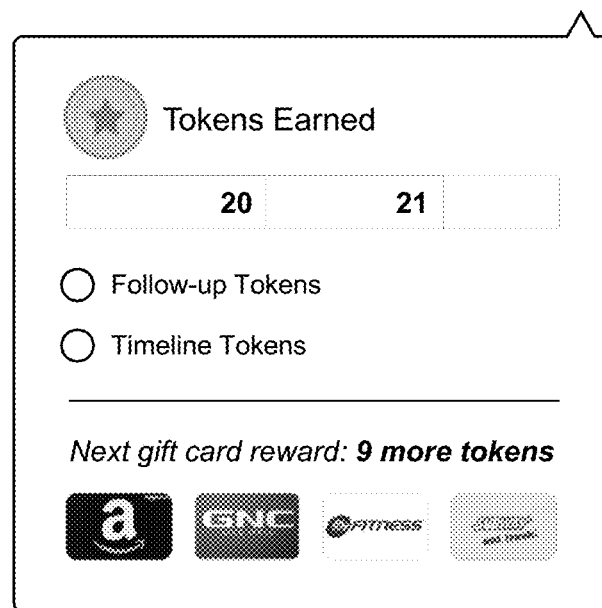
FIG. 6 provides an interface that shows a tally of the tokens earned by a staff member, consistent with some embodiments of the present invention.

FIG. 6 provides an interface 600 that shows a tally of the tokens earned by a staff member working with the healthcare provider seeing the patient in response to the staff member, for example, sending out OMDs to follow up after office visits (shown as follow-up tokens) and sending out OMDs according to a timeline or schedule (shown as timeline tokens). Interface 502 also includes a message indicating how many more incentives must be earned to reach the next reward (in this case 9 more tokens) along with a statement regarding an incentive such as a gift card or monetary reward.

Whether or not communication of the OMD is associated with a smart contract, A set of responses to the OMD may be received (step 420). It may then be determined whether the OMD includes and/or is associated with a smart contract (step 425). In most instances, this determination will depend upon whether the OMD is stored in the distributed ledger and/or on the blockchain. When the OMD is not stored in the distributed ledger or on the blockchain (e.g., stored in OMD database 145), it may not be associated with a smart contract. When the OMD does not include and/or is not associated with a smart contract, the set of responses received in step 420 may be packaged for storage on the blockchain (step 445). Execution of step 445 may include performance of a series of steps required to format and/or package the data included in the received set of steps and/or associated data (e.g., patient identity, patient account information, etc.) so that it is compatible with a blockchain and/or distributed ledger such as distributed ledger and/or blockchain 110. In some instances, execution of step 445 may further include combining the received set of responses with data received from other sources to fill a payload (e.g., payload 230) of a data block like data block 205 when, for example, the payload storage capacity of the data block into which the received set of responses is to be stored is not fully consumed by the received set of responses.

In some embodiments, execution of step 445 may include storage of the set of responses on a database (e.g., patient account database 120 and/or EMR database 125) and association (via, for example, a look up table) of the set of responses with a link (e.g., a hyperlink) or another pointer that may be stored on the blockchain and/or distributed ledger.

Optionally, in step 450, the set of responses and/or data block into which the set of responses is stored may be digitally signed using, for example, a digital signature of the computer executing process 400, the patient's identification, an identity of the computer system's operator. In many cases, the digital signature may include day/time information and may also include origination information for the data block and/or received set of responses. The set of responses and/or data block, which may be digitally signed when step 450 is executed, into which the set of responses are stored may then be broadcast, or otherwise communicated, to the blockchain and/or distributed ledger (step 455).

When the OMD includes a smart contract (step 425), it may then be determined whether the requirements of the smart contract are met (step 430). Exemplary smart contract requirements/parameters include, but are not limited to, viewership rights, editing rights, expiration rules, verification rules, and custom procedures. If not, then process 400 may proceed to step 445. If so, then the conditions dictated by the smart contract may be fulfilled or auto-executed (step 435). Step 445 may be executed following execution of step 435.

Optionally, in step 440, a patient account may be updated to reflect the status of the smart contract (e.g., whether the conditions have been fulfilled) and/or a message regarding a status of the smart contract and/or fulfillment thereof may be prepared and provided to the user and/or requester.

Figure 7A:
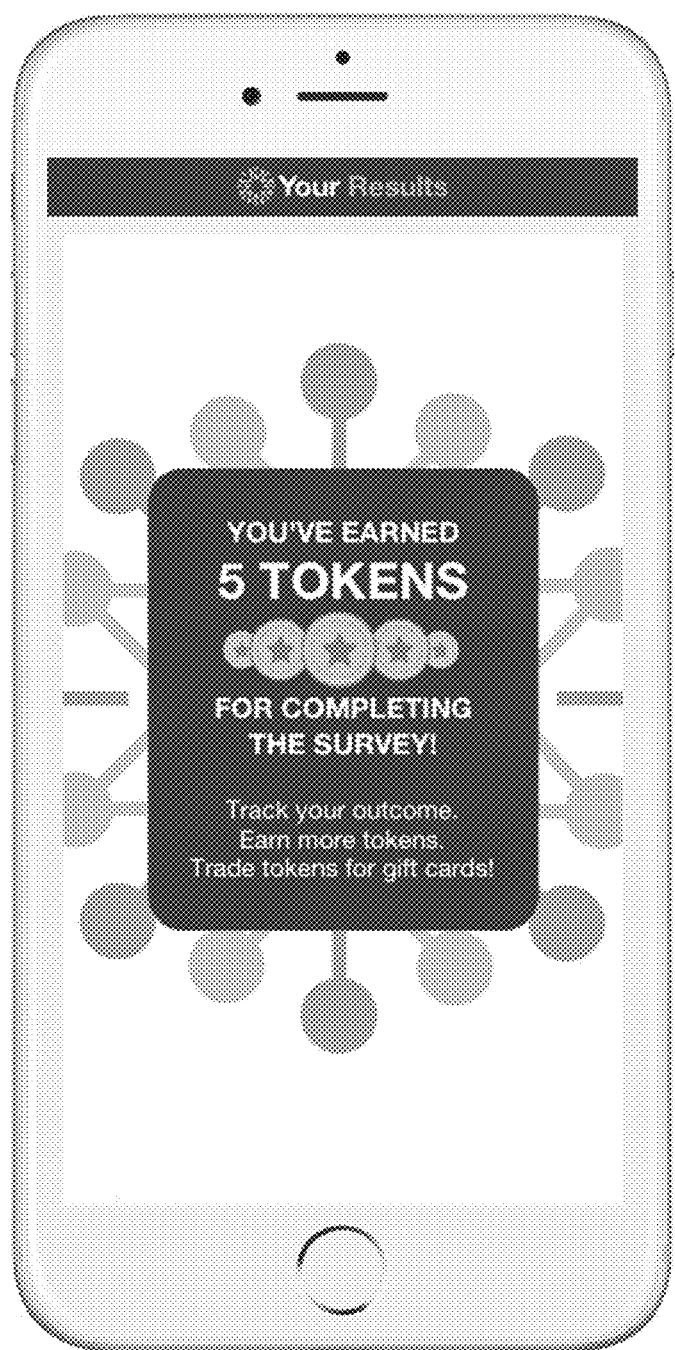
FIGS. 7A-7I provide screen shots of exemplary interfaces, consistent with some embodiments of the present invention.

FIGS. 7A-7I provide screen shots of exemplary interfaces that may be generated via execution of process 400 or portions thereof, particularly step 440. In FIG. 7A, a first interface 701 is provided. First interface 701 provides a message indicating that the status of a smart contract (i.e., "you've earned 7 tokens for completing the survey").

Figure 7B:
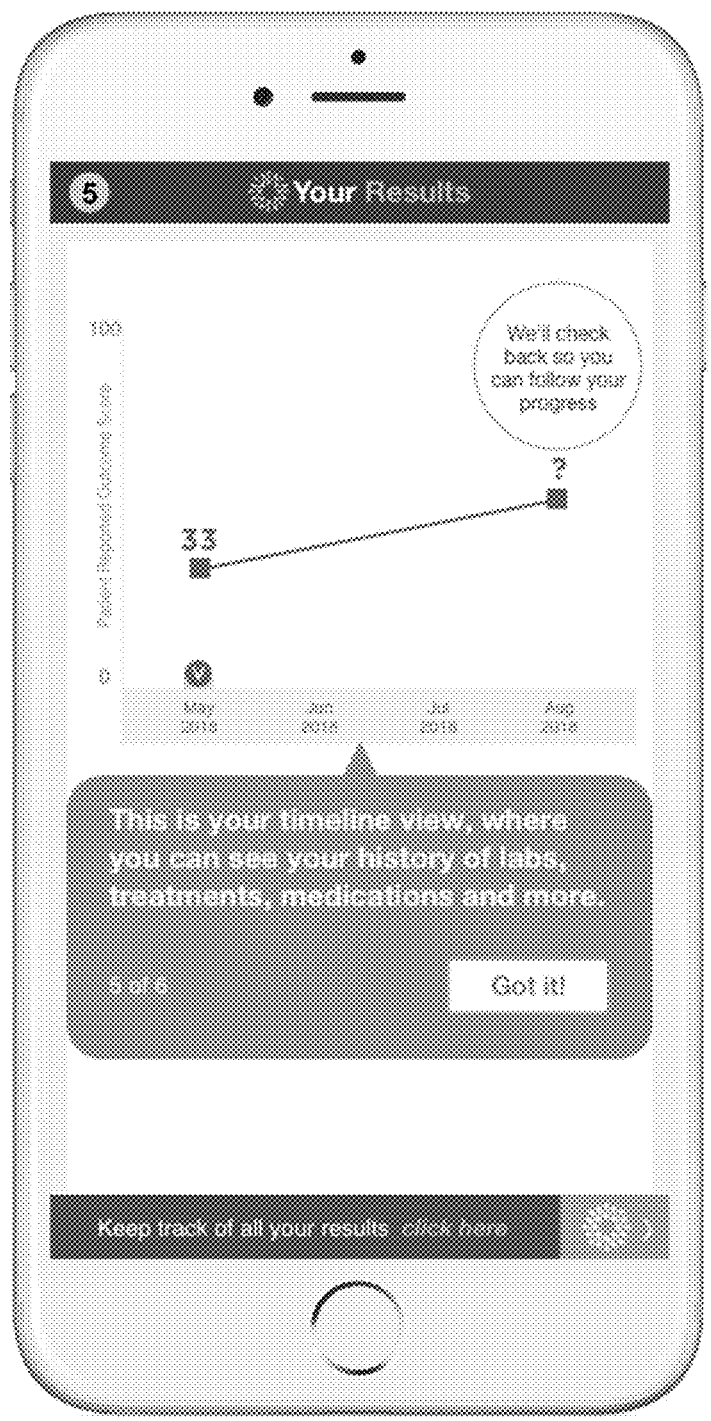
Figure 7C:
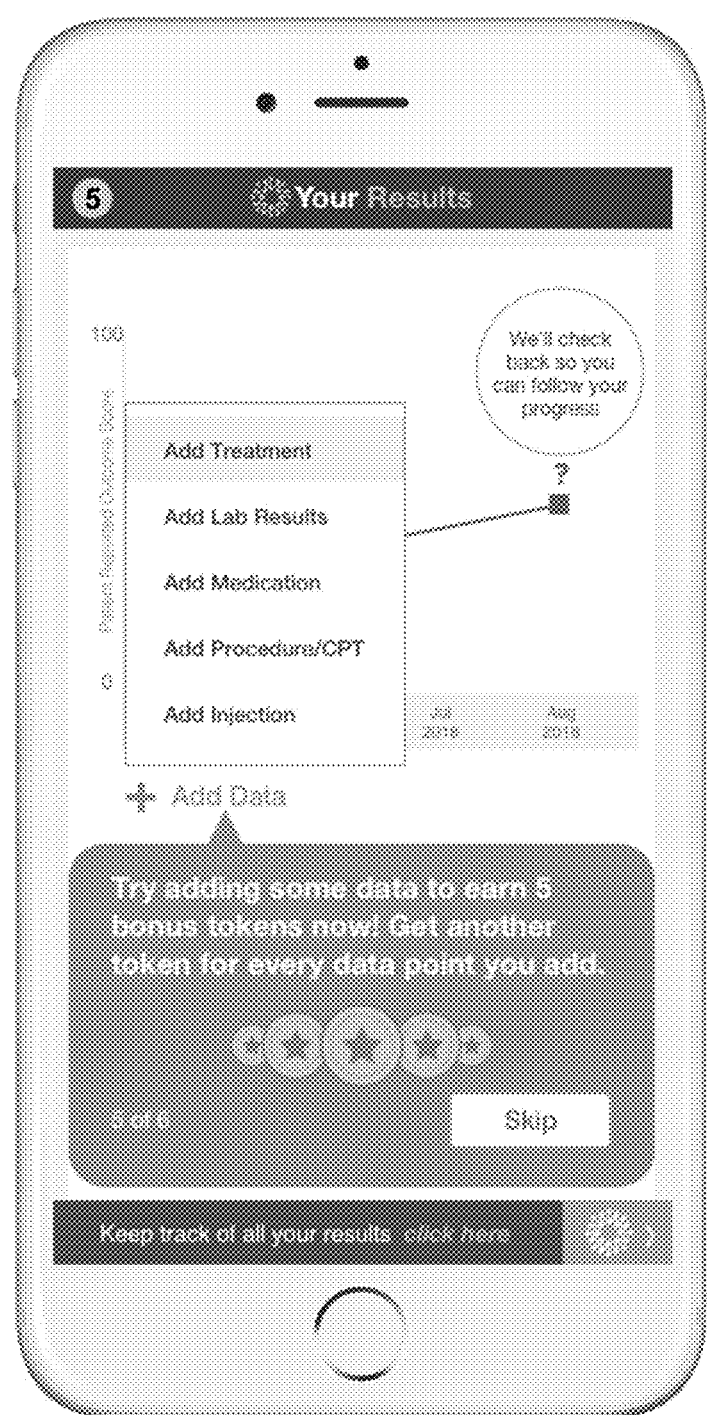
Figure 7D:
Figure 7E:
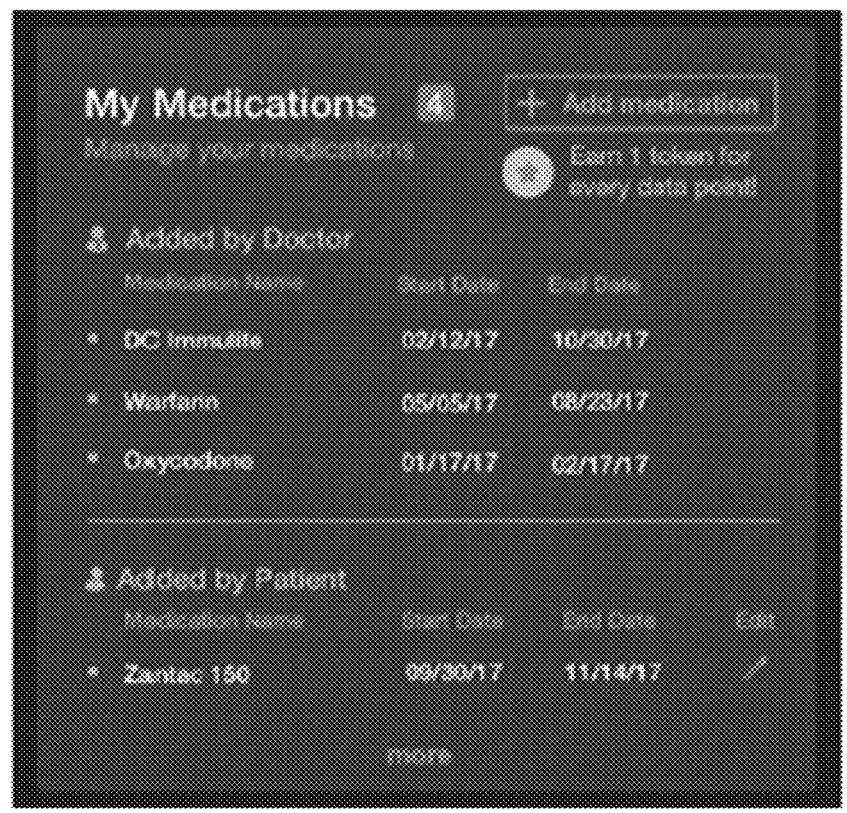
Figure 7F:
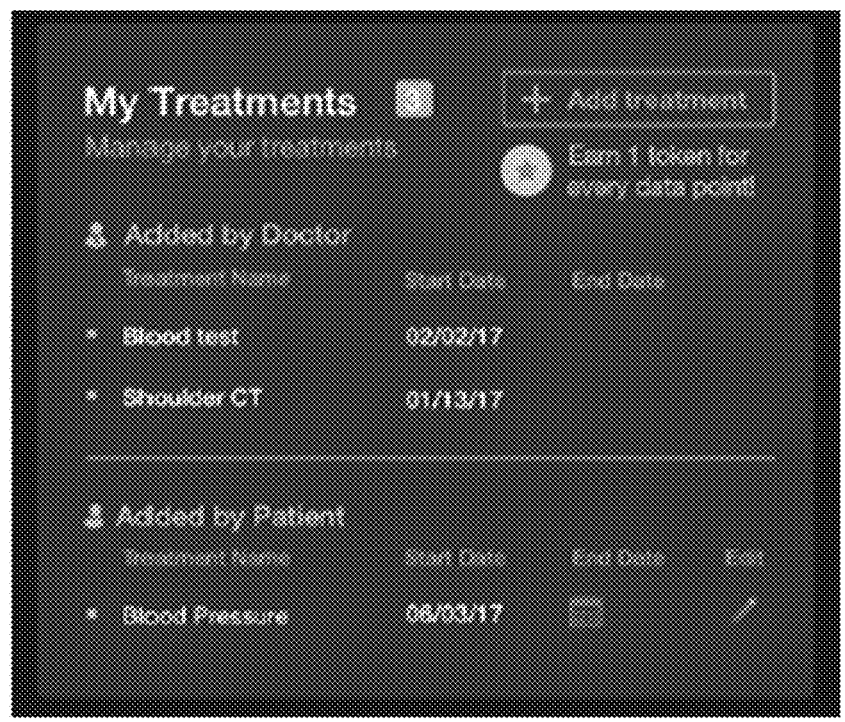
Figure 7G:
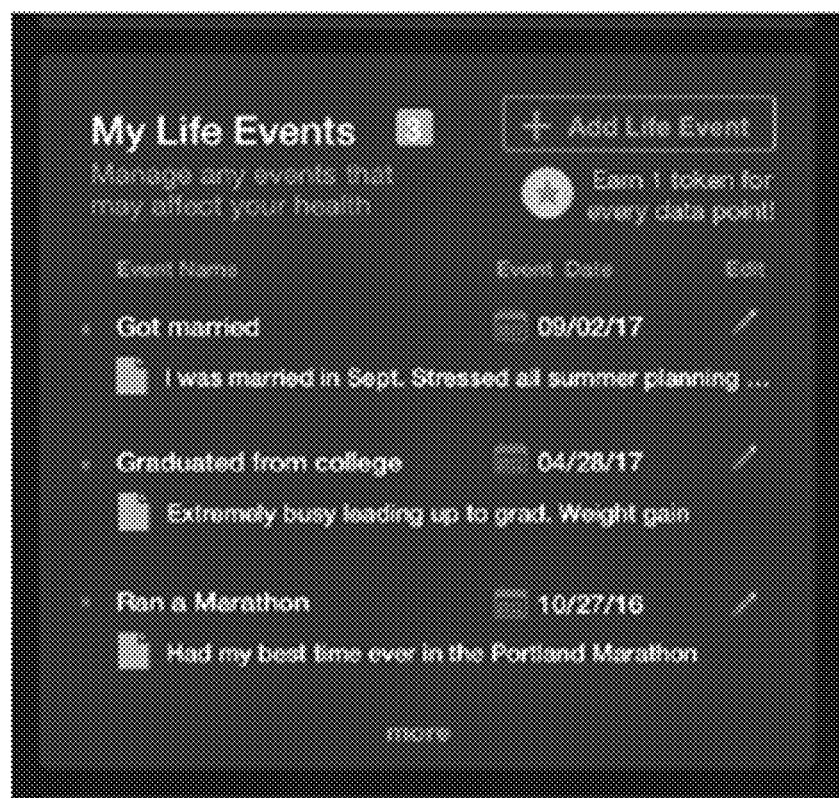
Figure 7H:
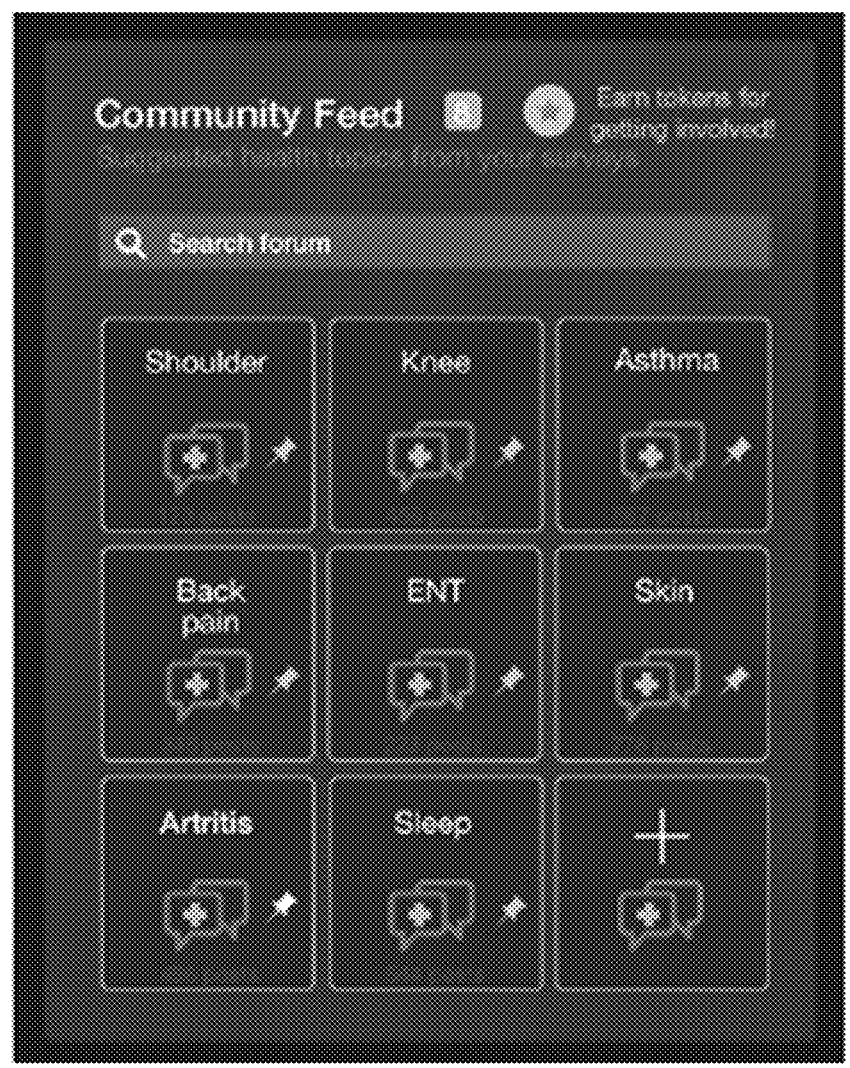
Figure 7I:
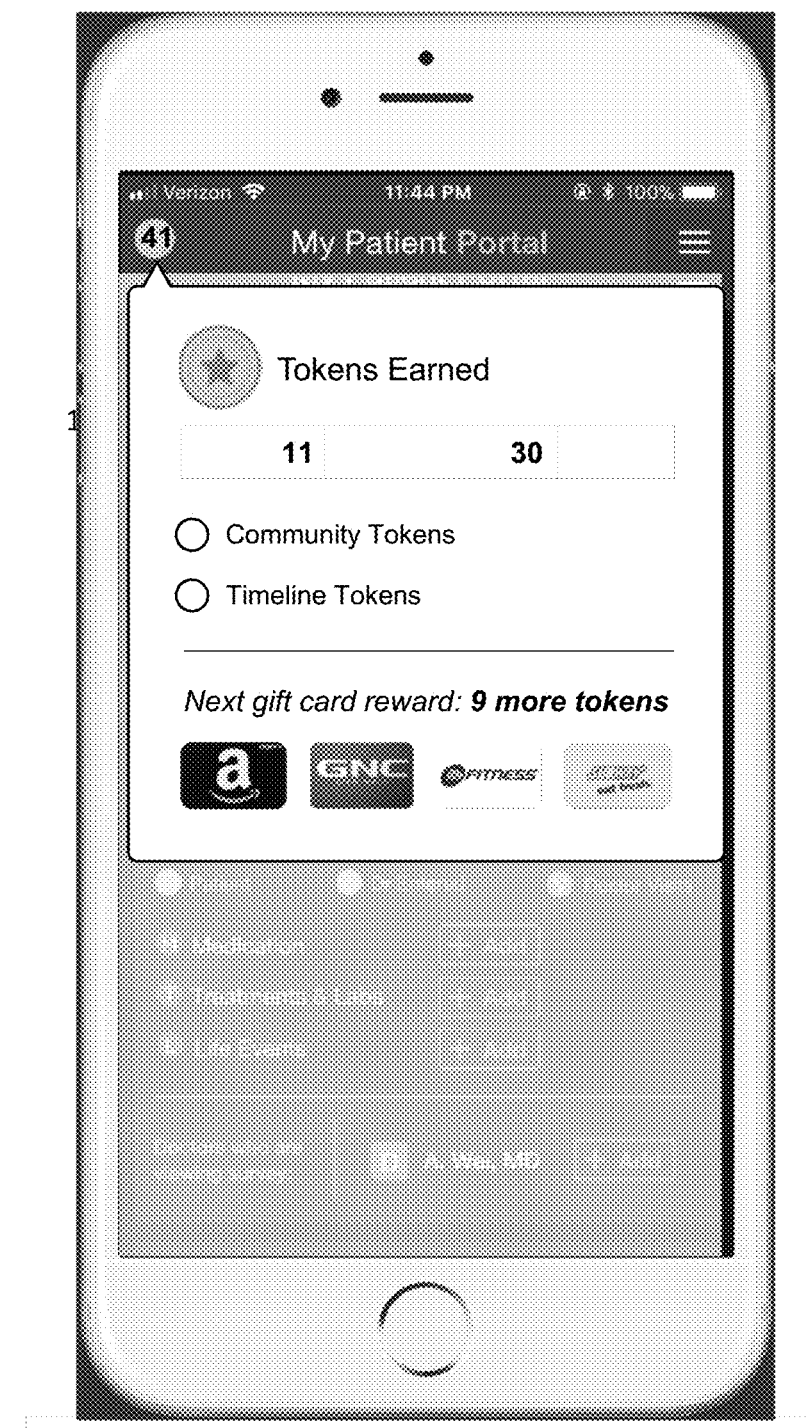

FIGS. 7B and 7C provide a second interface 702 and a third interface 703, respectively. In second interface 702, a patient's wellness score or other information associated with his or her patient account is displayed along with a message providing information regarding the content displayed via second interface 702. Third interface 703 provides a message to the patient with information regarding one or more terms of a smart contract (i.e., earn tokens by entering data).

FIGS. 7D-7I provide a series of interfaces 704-709 by which a patient may interact with his or her patient account and fulfill conditions of one or more smart contracts. Interface 704 provides a series of icons associated with doctors the patient has a relationship with and a message regarding terms of a smart contract the patient may fulfill by looking for a doctor. Interface 705 provides a list of medications prescribed for the patient by a doctor and/or self-prescribed and a message regarding terms of a smart contract the patient may fulfill by entering information regarding medication they are taking into his or her patient account. Interface 705 provides a list of treatments prescribed for the patient by a doctor and/or self-prescribed and a message regarding terms of a smart contract the patient may fulfill by entering information regarding the treatment(s) into his or her patient account. Interface 707 provides a list of life events entered by the patient and a message regarding terms of a smart contract the patient may fulfill by entering information regarding life events into his or her patient account. Interface 708 provides a list of community feeds (e.g., a message board or blog regarding a particular diagnosis, disease, treatment, etc.) the patient is associated with and a message regarding terms of a smart contract the patient may fulfill by interacting with and/or entering information regarding a community feed. Interface 709 provides a tally of incentives (i.e. tokens) earned via fulfilment of one or more smart contracts and what the incentives may be converted to (i.e., a gift card to a retail establishment. A patient may earn or receive a token when, for example, responding to an OMD, inputting data into his or her patient account, participating in a community feed, communicating with other patients via the patient account and/or a community feed, looking for information regarding a doctor, treatment, or diagnosis, etc.

Figure 8:
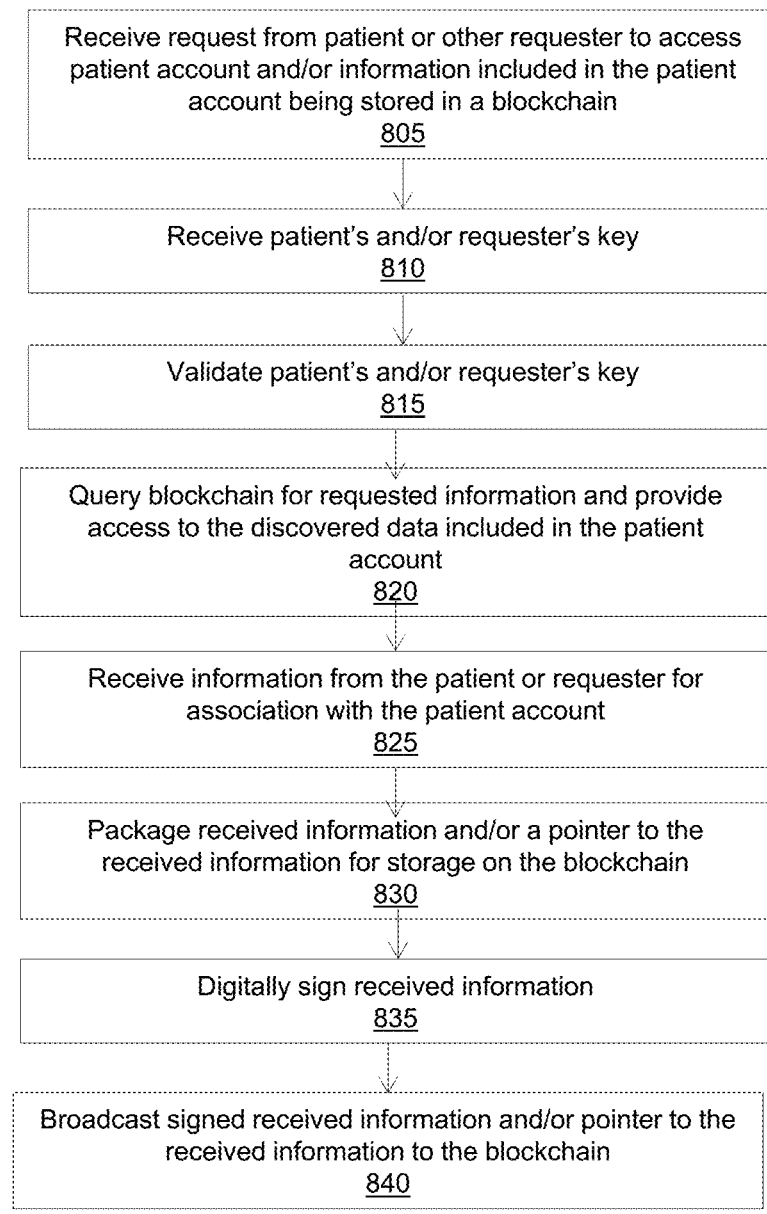
FIG. 8 provides a flowchart of an exemplary process for providing access to information associated with a patient account that may not be stored on a blockchain and optionally receiving information from the patient or other requester and broadcasting the received information for storage on a blockchain and/or distributed ledger, consistent with some embodiments of the present invention.

FIG. 8 provides a flowchart of an exemplary process 800 for providing access to information associated with a patient account that may not be stored on a blockchain and optionally receiving information from the patient or other requester and broadcasting the received information for storage on a blockchain and/or distributed ledger. Process 800 may be executed by, for example, system 100, system 101, or any component thereof.

Initially, in step 805, a request to access a patient account and/or information included in, or otherwise associated with, a patient account stored in a blockchain and/or distributed ledger (e.g., distributed ledger and/or blockchain 110) may be received from, for example, a patient or other requester (e.g., healthcare provider, caregiver, etc.) via communication between an electronic device like user device 155 and a computer like computers A-N 105A-105N.

Then, in step 810, a patient's and/or requester's key may be received by, for example, a computer like computer A 105A-computer N 105N. In some cases, the key may be a password. In additionally, or alternatively, the key may be a cryptographic key stored on the patient's device that is communicated to, for example, a server providing or administrating the patient account that is accessed and/or activated when the patient signs into his or her patient account (via, for example, entry of a password).

The patient's and/or requester's key may then be verified (step 815). Typically, this step is performed by the computer facilitating execution of step 805 and 810 but, this need not be the case. If the patient's and/or requester's key is not verified, execution of process 800 may end.

Upon verification of the patient's and/or requester's key, the blockchain and/or distributed ledger may be queried for the information requested in step 805 and access to the to the discovered data may be provided via, for example, communication of the discovered data to a user device like user device 110 (step 820).

Optionally, in step 825, information regarding the patient may be received for inclusion in the patient account from, for example, the patient and/or the requester. The received information may then be packaged for storage on the distributed ledger and/or blockchain (step 830). Often, this packaging will include time stamping the received information. In some embodiments, packaging of the received information may include storage of the received information on a database (not on the blockchain) such as patient information database 120 and/or EMR database 125 and then associating the location of the stored received information with a link or pointer that may be packaged for storage on the blockchain. In some instances, packaging the received information may include digitally signing the received information using, for example, the patient's and/or requester's key and/or identification information for the user device (e.g., a SIM card number) (step 835). The packaged received information and/or a pointer thereto then be broadcast, or otherwise communicated, to the blockchain and/or distributed ledger for storage thereon (step 840).

Figure 9:
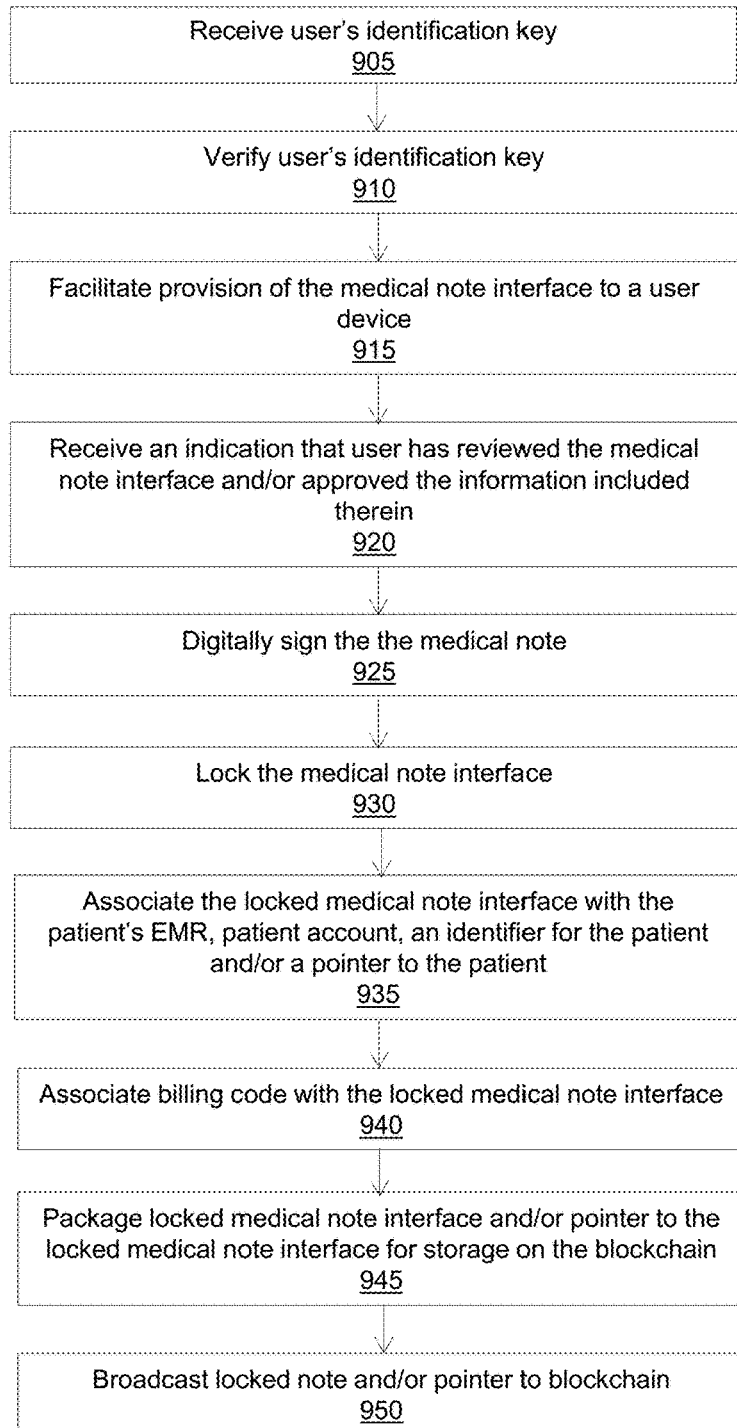
FIG. 9 provides a flowchart of an exemplary process for providing access to a medical note interface and optionally receiving information from the user regarding the medical note interface and broadcasting the received information for storage on a distributed ledger and/or blockchain, consistent with some embodiments of the present invention.

FIG. 9 provides a flowchart of an exemplary process 900 for providing access to a medical note interface and optionally receiving information from the user regarding the medical note interface and broadcasting the received information for storage on a distributed ledger and/or blockchain. Process 900 may be executed by, for example, system 100, system 101, or any component thereof. Further information regarding medical note interfaces is provided in U.S. Provisional Patent Application No. 62/622,020, which is hereby incorporated by reference in its entirety herein.

Initially, in step 905, a user's identification key may be received as part of, for example, the user signing into a medical note interface software application and/or a request to access information associated with a patient account. The user's identification key may then be verified (610) and provision of the medical note interface may be facilitated (step 915). If the user's identification key cannot be verified, execution of process 900 may end. In some instances, when some, or all of patient account information associated with a patient for whom the medical note interface pertains, is stored in a blockchain and/or distributed ledger (e.g., distributed ledger and/or blockchain 110) on a blockchain, execution of step 915 may include extracting patient account information from the blockchain and/or distributed ledger and formatting it for display on the medical note interface.

The medical note interface may display of variety of types of information regarding one or more patients (typically only one patient) including, but not limited to, patient name, patient's medical history, treatments the patient has undergone or is scheduled to undergo, treatment compliance information, and medical diagnoses. In some cases, electronic medical record information provided by a medical note interface may be subject to one or more filters or permissions as may be set up by, for example, the patient, a caregiver, and/or a provider different from the provider currently viewing the medical note interface. In some instances, information provided by the medical note interface may be specific to a particular situation (e.g., chief complaint) or diagnosis as may be the case when the patient is communicating with a provider (e.g., in the provider's office or via a tele-medicine encounter) regarding a particular complaint for diagnosis. For example, a patient may choose to limit access to his or her mental/behavioral medical information to providers who are directly involved in caring for this aspect of the patient's health such that when, for example, the patient goes to the emergency room with a broken ankle, the tending provider cannot access this information. Limiting the information provided by a medical note interface may be done for many reasons including, but not limited to, protecting the privacy of the patient, prioritizing information provided by the medical note interface so that information deemed relevant to the particular situation prompting display of the medical notes interface is more prominently displayed, and/or removing extraneous information that may not be relevant to user so as to, for example, facilitate an efficient user experience with the medical note interface.

Next, an indication that the user has reviewed the medical notes interface and/or approved the information included therein may be received (step 920). Execution of step 920 may be facilitated by, for example, the user selecting one or more icons or other graphic objects provided by the medical notes interface and/or the users signing the medical interface via entry of, for example, the password, username, a digital signature, biometric information (e.g., fingerprint or eye scan), and the like.

Optionally, the medical note may be digitally signed (step 925) using, for example, the user's key, treatment facility information/identifier, and/or administrator credentials, and/or user device identification information (e.g., SIM card number). Once the medical note interface has been reviewed (step 920) and/or signed (step 925), it (or patient-specific information associated therewith) may be locked to, for example, prevent any further modification of the information included thereon and/or associated therewith (step 930).

In step 935, the locked medical note interface (or patient-specific information associated therewith) may be associated with the patient's EMR and/or patient account via, for example, association of the locked medical note interface (or patient-specific information associated therewith) with an identifier for the patient, the patient's EMR, the patient's account, a pointer to the patient, and/or a pointer to the patient's account.

Optionally, a billing code may be associated with the locked medical note interface (step 940). Exemplary ways to execute step 940 may be to determine an amount and complexity of medical decision-making data reviewed in the medical note interface and/or time spent reviewing the medical note interface and/or with the patient during a consultation relating to the information displayed on the medical note interface, accessing a set of rules corresponding to billing codes and rules (e.g., and E&M codes), and determining a corresponding billing code.

In step 945, the locked medical note interface (or patient-specific information associated therewith) may be packaged for storage on the distributed ledger and/or blockchain and, in step 950, the packaged locked note may be broadcast to the blockchain and/or distributed ledger. In some embodiments, packaging of the locked medical note interface (or patient-specific information associated therewith) may include storage of the locked medical note interface (or patient-specific information associated therewith) on a database (not on the blockchain) such as patient information database 120 and/or EMR database 125 and then associating the location of the stored locked medical note interface (or patient-specific information associated therewith) with a link or pointer that may be packaged for storage on the blockchain.

Figure 10:
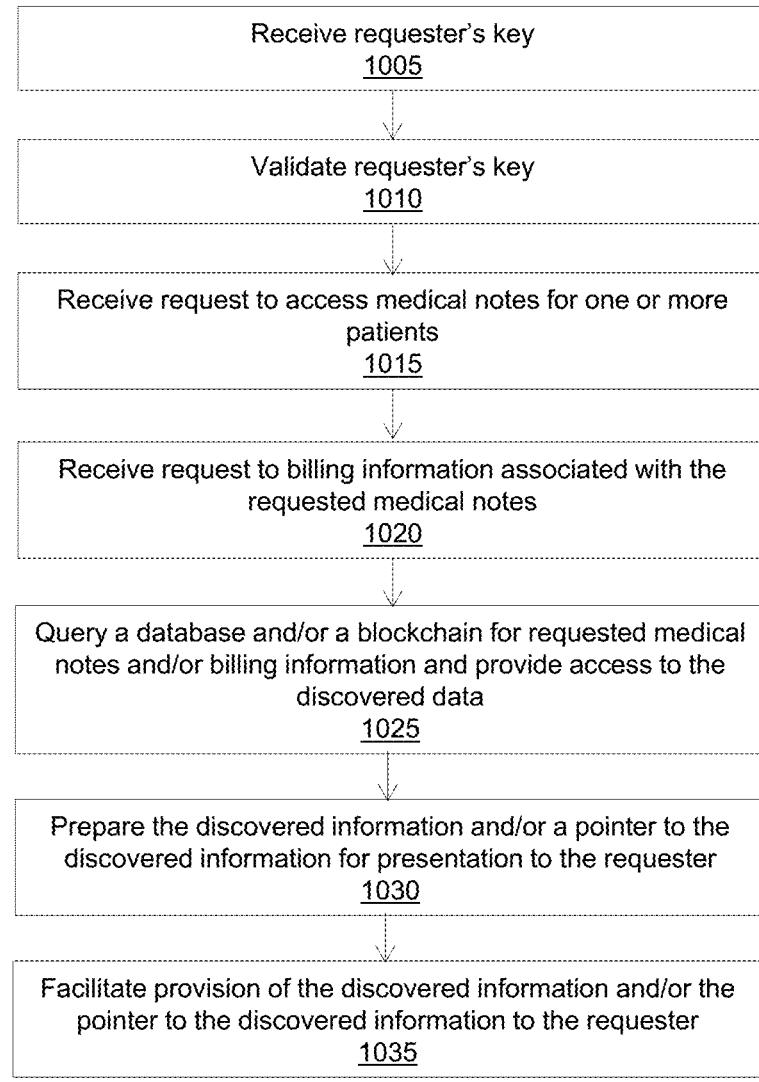
FIG. 10 provides a flowchart of an exemplary process for providing access to a plurality of medical notes and, in some instances, billing information associated with the medical notes, consistent with some embodiments of the present invention.

FIG. 10 provides a flowchart of an exemplary process 1000 for providing access to a plurality of medical notes and, in some instances, billing information associated with the medical notes. Process 1000 may be executed by, for example, system 100, system 101, or any component thereof.

In step 1005, a requester's key may be received. Exemplary requesters include, but are not limited to, administrators, accountants, billing coordinators, auditors, local, state, and/or federal governmental agencies (e.g., CMS, Medical, etc.), and third-party reviewing agencies (e.g., U.S., News and World Report Magazine). The requester's key may then be validated (step 1010). If the requester's key cannot be validated, execution of process 1000 may end.

In step 1015, a request to access medical notes for one or more patients may be received. Optionally, and step 1020, a request to receive billing information associated with the requested medical notes may also be received. One or more databases, and/or distributed ledgers, and/or blockchains that store medical notes, patient account information, electronic medical records, and/or billing information may then be accessed and queried for the requested information (step 1025).

In step 1030, the discovered information may then be prepared for presentation to the requester. In some instances, execution of step 1030 may include formatting the discovered information in a preferred format (e.g., spreadsheet or word processing document), anomizing the data or otherwise removing personally identifiable information from the data, filtering the data so that it includes information relating to billing and accounting issues without include specific medical information such as duration of an office visit, complexity of medical decision making data considered, tests performed during an office visit, billing code(s) associated with a medical note, and/or historical data for a particular provider or patient. In some embodiments, preparing the discovered information may include preparing a pointer to the discovered information (e.g., extracting a pointer to the discovered information from the distributed ledger and/or blockchain). In step 1035, provision of the discovered information and/or a link thereto to the requester may then be facilitated (step 1035).

In some embodiments, process 1000 may be executed as part of performing an internal or external audit of, for example, services provided to patients and/or how those services were billed or reported to, for example, a governmental agency or in a legal, financial, or corporate document associated with a provider of the medical services underlying the medical notes accessed. Additionally, or alternatively, process 1000 may be executed to assess staffing needs or performance metrics for various providers of medical and healthcare services.

Figure 11:
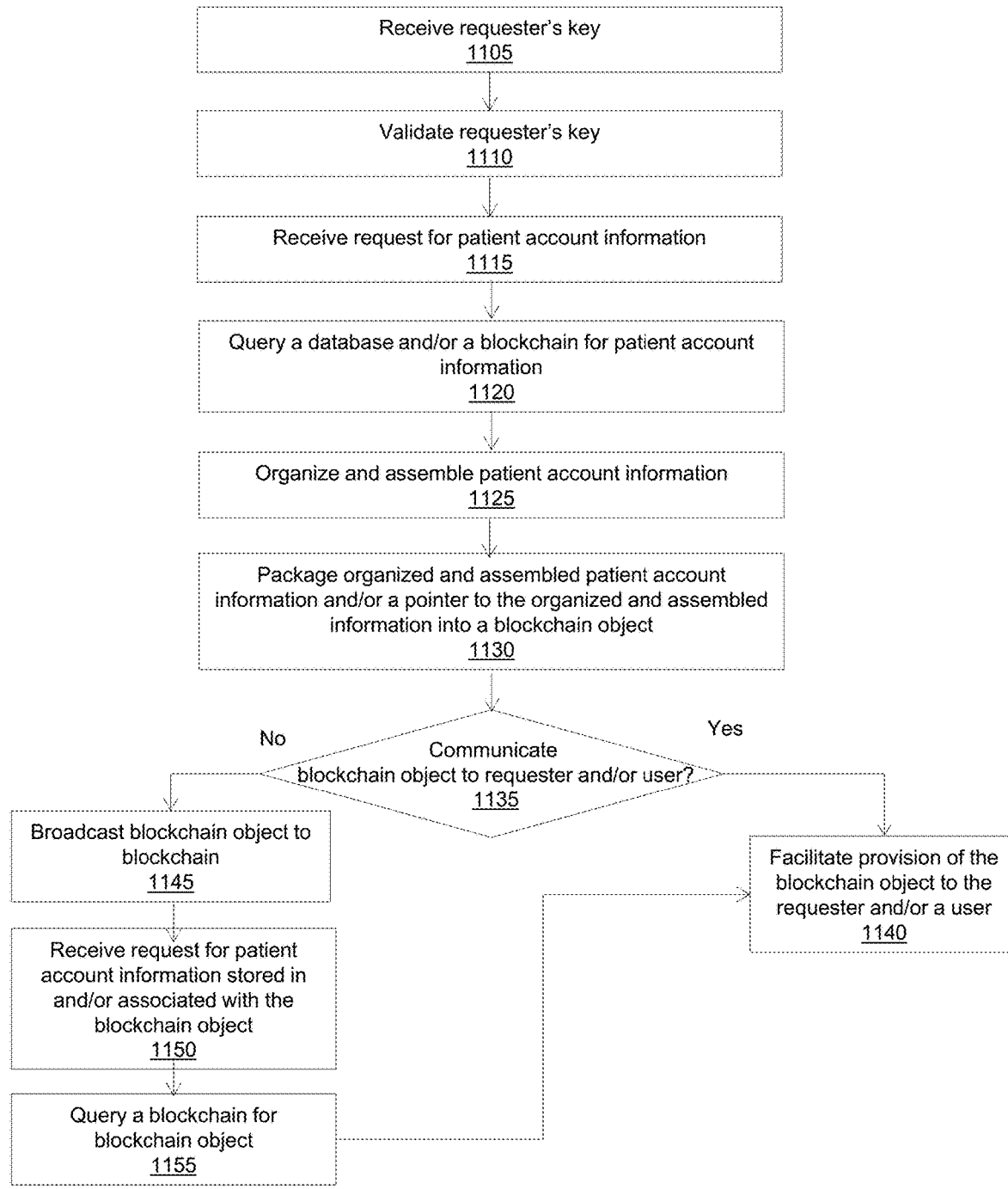
FIG. 11 provides a flowchart of an exemplary process for facilitating provision of a blockchain object including patient account information, consistent with some embodiments of the present invention.

FIG. 11 provides a flowchart of an exemplary process 1100 for facilitating provision of a blockchain object including patient account information. Process 1100 may be executed by, for example, system 100, system 101, or any component thereof.

In step 1105, a requester's key may be received and in step 1110 that key may be validated. If the requester's key cannot be validated, process 1100 may end. A requester may be, for example, a patient associated with the patient account, a provider, a treatment facility administrator, and/or an auditor. A request for patient account information may then be received (step 1115). In some embodiments, step 1115 may be performed prior to steps 1105 and/or step 1110. For example, a request for a requester's key may be provided to the requester responsively to receiving a request for patient information (i.e., step 1105). At times, the request may include one or more parameters or qualifiers for the requested patient account information. Exemplary parameters include, but are not limited to, features or characteristics of the patient (e.g., age, race, diagnosis, etc.), a time period (e.g., entire medical history, last ten years, history since a treatment, etc.), patient information related to a treatment and/or diagnosis, and so on.

A blockchain and/or distributed ledger, such as distributed ledger and/or blockchain 110, may then be queried for the requested patient information (step 1120). The database may be maintained by, for example, an entity managing or storing the patient account. At times, multiple databases and/or distributed ledgers may be queried. In step 1125 the retrieved patient account information may be organized (e.g., chronologically, by diagnosis, etc.) and assembled so that the organized and assembled patient account information and/or a pointer thereto may be packaged into a blockchain object or data block similar to, for example, data block 205 (step 1130). An advantage to this step and/or execution of steps 1105-830 may be the consolidation and/or organization of a patient's account information from multiple sources to facilitate, for example, secure communication of the patient account information and/or assist with efficient storage of same.

Optionally, in step 1135, it may be determined whether to communicate the blockchain object directly to the requester and/or a user or third party (e.g., provider, treatment facility, etc.) and, if so, provision of the blockchain object to the requester and/or another user may be directly communicated (step 1140) by, for example, transmission of the blockchain object to the requester/user and/or allowing the requester/user to access the blockchain object via, for example, a portal or other interface. In some instances, the requester may want someone other than him or herself to have access to the patient account information included in the blockchain object as may be the case when the requester is a patient and he or she wishes to provide the patient account information included in the blockchain object to another. Alternatively, in another embodiment, the requester may be a provider or administrator wanting to communicate the patient account information included in the blockchain object to the patient him or herself. This may be done for a variety of reasons including, but not limited to, managing data (as may be necessary when changing computer hardware/databases), performing an audit, updating a system, and/or onboarding one or more new patients into the system (as may happen when a doctor with a set of patients changes medical facilities).

When the blockchain object is not to be directly communicated to the requester and/or user, the blockchain object may be broadcast to a distributed ledger, like distributed ledger and/or blockchain 110, for storage thereon (step 1145). In some instances, step 1145 may be performed when the decision at step 1135 is yes. This may occur when, for example, it is desirable for the blockchain object to be directly communicated to the requester and/or user and stored on the blockchain and/or distributed ledger.

In step 1150 a request or the patient account information stored in and/or associated with (via, for example, a pointer) the blockchain object may be received. In some instances, execution of step 1150 may be followed be receipt of the requester's key and verification thereof. Then, the blockchain and/or distributed ledger may be queried for the blockchain object (step 1155) and the provision of the discovered blockchain object to the requester and/or user may then be facilitated (step 1140).

Figure 12:
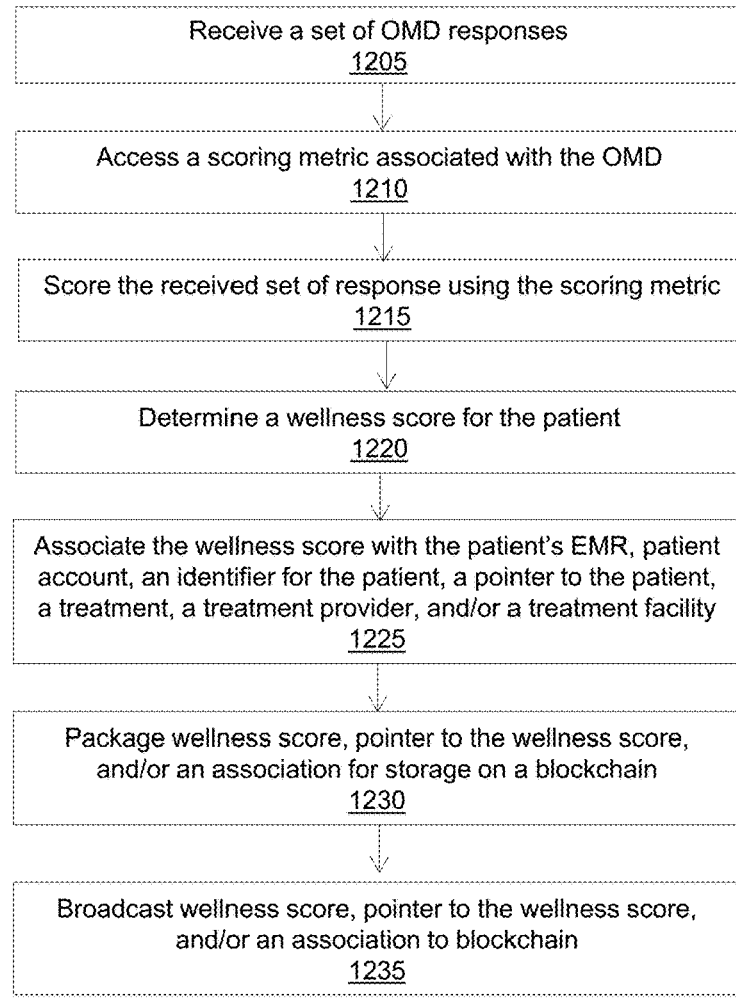
FIG. 12 provides a flowchart of an exemplary process for determining a wellness score and broadcasting the wellness score to a blockchain and/or distributed ledger, consistent with some embodiments of the present invention.

FIG. 12 provides a flowchart of an exemplary process 1200 for determining a wellness score and broadcasting the wellness score to a blockchain and/or distributed ledger. Process 1200 may be executed by, for example, system 100, system 101, or any component thereof.

In step 1205, a set of OMD responses may be received from, for example, a patient and/or responsively to a query for a set of OMD responses. When received responsively to a query, the query for the set of OMD responses may be a query of a blockchain stored on a blockchain and/or distributed ledger like distributed ledger and/or blockchain 110. In some instances, the set of OMD responses received in step 1205 may be the same as the set of OMD responses received in step 420 of process 400.

In step 1210, a scoring metric associated with the OMD may be accessed. In one embodiment, step 1210 may be executed by server B 170 querying a database that stores OMD scoring metrics, such as OMD database 145. Exemplary scoring metrics include but are not limited to normalization procedures, baseline values for responses to one or more questions posed by and/or data points associated with the OMD, weighting values for to one or more questions posed by and/or data points associated with the OMD, and so on. The set of responses may then be scored using the scoring metric (step 1215) and a wellness score for the patient with him the set of responses associated may be determined (step 1220). The wellness score may be determined on any appropriate scale (e.g., 1-10, 1-100, etc.)

Optionally, in step 1225, the wellness score may be associated with, for example, the patient's EMR, the patient's account, an identifier for the patient, a pointer to the patient, a treatment the patient has undergone, a treatment provider for the patient, and/or a treatment facility for the patient.

Figure 13:
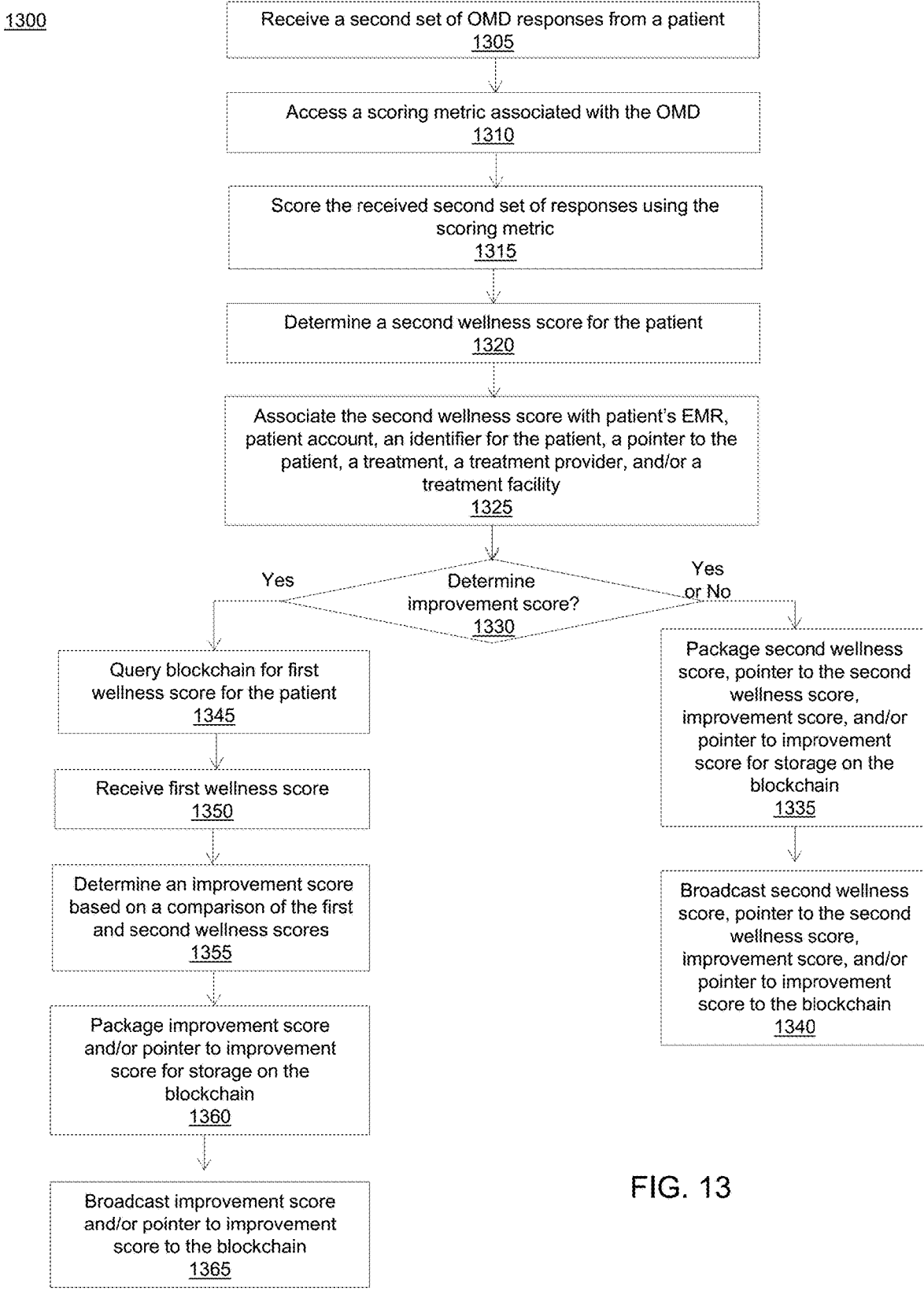
FIG. 13 provides a flowchart of an exemplary process for determining a second wellness score and an improvement score and broadcasting the second wellness score and/or an improvement score to a distributed ledger and/or blockchain, consistent with some embodiments of the present invention.

FIG. 13 provides a flowchart of an exemplary process 1300 for determining a second wellness score and an improvement score and broadcasting the second wellness score and an improvement score to a distributed ledger and/or blockchain like distributed ledger/blockchain 110. Process 1300 may be executed by, for example, system 100, system 101, or any component thereof.

In step 1305, a second sent of OMD responses may be received from a patient in a manner similar to, for example, the way the set of OMD responses was received in step 1205. The second set of OMD responses may be received in response to a second communication of the OMD to patient as part of, for example, a follow up to a treatment, office visit, and/or general health inquiry. In many instances, the second set of responses will be received at some point later in time (i.e., after) relative to the first set of responses being received.

Then, in step 1310, a scoring metric associated with the OMD may be accessed and the second set of responses may be scored using the accessed scoring metric (step 1315). Execution of step 1310 and 1315 may resemble execution of steps 1210 and 1215, respectively. Optionally, in step 1325, the second wellness score may be associated with, for example, the patient's EMR, the patient's account, an identifier for the patient, a pointer to the patient, a treatment the patient has undergone, a treatment provider for the patient, and/or a treatment facility for the patient.

In step 1330, it may be determined whether or not an improvement score for the patient is to be determined. When an improvement score is being calculated, the blockchain and/or distributed ledger may be queried for a first wellness score (as may be determined via execution of process 1200) for the patient stored on the blockchain (step 1345). When the first wellness score is received (step 1350), an improvement score for the patient may be determined by comparing the first and second wellness scores. When the improvement score is positive, it may indicate that the patient's heath has gotten better and/or that they are responding positively to treatment. When the improvement score is negative, it may indicate that the patient's heath has declined and/or that they are responding negatively to treatment. The improvement score may be a numerical score and, at times, may be represented as a percentage. The determined improvement score may then be packaged for storage on a blockchain (step 1360) and broadcast to a blockchain and/or distributed ledger, like distributed ledger and/or blockchain 110, for storage thereon (step 1365).

Whether or not an improvement score is to be determined, second wellness score, a pointer to the second wellness score, and/or one or more of the associations performed in step 1325 may be packaged for storage on a blockchain (step 1335) and broadcast to a blockchain and/or distributed ledger, like distributed ledger and/or blockchain 110, for storage thereon (step 1340).

Figure 14:
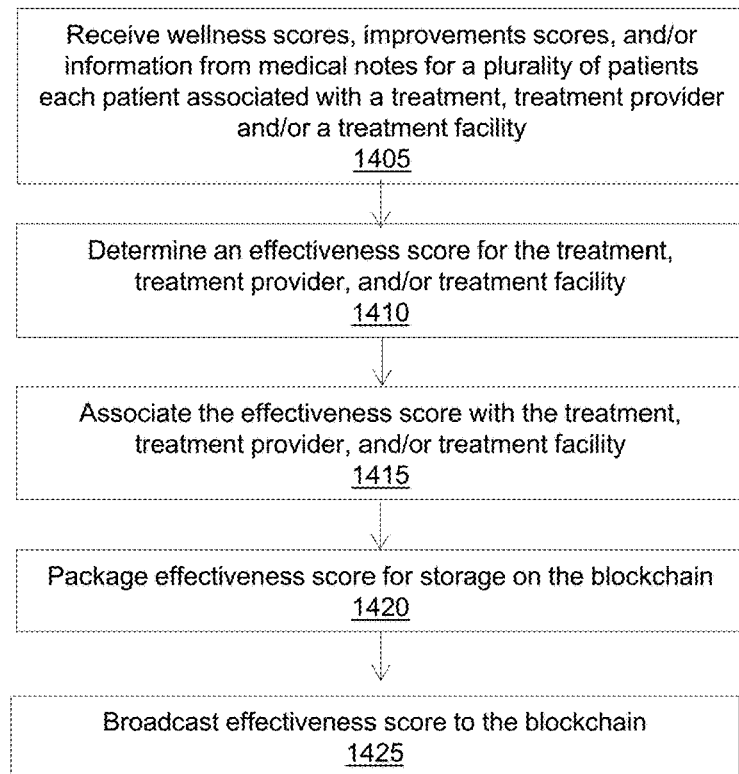
FIG. 14 provides a flowchart of an exemplary process for determining an effectiveness score, consistent with some embodiments of the present invention.

FIG. 14 provides a flowchart of an exemplary process 1400 for determining an effectiveness score. Process 1400 may be executed by, for example, system 100, system 101, or any component thereof.

Initially, wellness scores, improvements scores, and/or information from medical notes for a plurality of patients may be received. In some embodiments, one or more of the wellness scores, improvements scores, and/or information from medical notes may be received from a blockchain and/or distributed ledger. Each patient, wellness score, improvement score, and/or medical note may be associated with one or more of a treatment, treatment provider, and/or a treatment facility. In some instances, the information received in step 1405 will be indexed or cross referenced with different identifiers including, but not limited to, diagnostic codes, treatment codes, billing codes, treatment providers, treatment facilities, patient demographic information, concurrent treatments, and so on.

In step 1410, an effectiveness score for the treatment, treatment provider, and/or treatment facility may be determined using the information received in step 1405. The effectiveness score may be determined using a variety of metrics and/or scoring procedures. For example, in an embodiment where an effectiveness score is determined for a treatment provider, wellness scores, improvements scores, and/or information from medical notes for a plurality of patients undergoing a particular treatment and under the care of a particular treatment provider may be analyzed to determine how effective the treatment provider is at providing treatment. This may include aggregating the wellness and/or improvement scores for patients under the care of the treatment provider and comparing them to a baseline or benchmark value to see how well their patients respond to treatment compared with the baseline or benchmark.

In another example, an effectiveness score is determined for a particular treatment (typically associated with a diagnosis or medical condition) and wellness scores, improvements scores, and/or information from medical notes for a plurality of patients undergoing the particular treatment may be analyzed to determine how effective the treatment is at treating the diagnosis or medical condition. This may include aggregating the wellness and/or improvement scores for patients undergoing the treatment and comparing them to a baseline or benchmark value for the treatment or other treatments for the diagnosis or medical condition to see how well patients respond to treatment compared with the baseline or benchmark.

The effectiveness score may then be associated with the treatment provider, treatment facility, and/or treatment (step 1415) by, for example, indexing the effectiveness score for storage in a database like database OMD database 145. The effectiveness score may then be packaged for storage on the blockchain (step 1420) and broadcast to a blockchain and/or distributed ledger, like distributed ledger and/or blockchain 110, for storage on a blockchain (step 1425).

Figure 15:
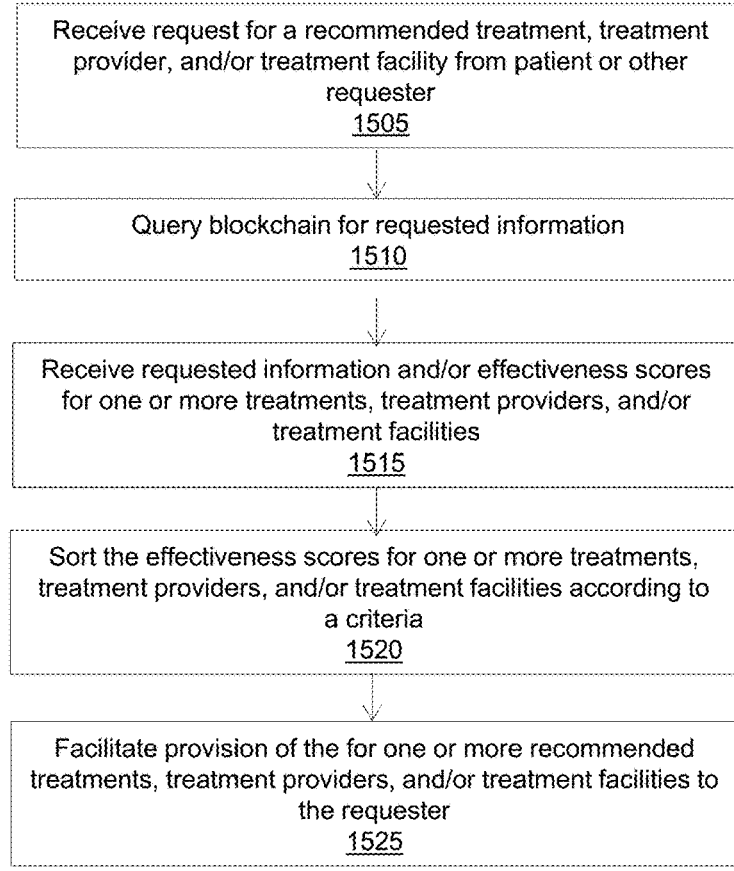
FIG. 15 provides a flowchart of an exemplary process for providing recommended treatments, treatment providers, and/or treatment facilities to a requester, consistent with some embodiments of the present invention.

FIG. 15 provides a flowchart of an exemplary process 1500 for providing recommended treatments, treatment providers, and/or treatment facilities to a requester. Process 1500 may be executed by, for example, system 100, system 101, or any component thereof.

Initially, a request for a recommended treatment, treatment provider, and/or treatment facility may be received from, for example, a patient or other requester (e.g., doctor or care taker) (step 1505). The request may include one or more characteristics or criteria including, but not limited to, demographic information, vital statistics, and/or comorbidities, geographic preferences, gender preferences, and/or allergies for the patient. A blockchain and/or distributed ledger may then be queried to extract the requested information and/or information needed to provide a recommendation (step 1510). In step 1515, the requested information and/or effectiveness scores associated with the request may be received. The effectiveness scores may then be sorted according to the content of the request and/or the received information (step 1520). The treatments, treatment providers, and/or treatment facilities associated with the sorted effectiveness scores may then be provided to the requester (step 1525). In one example, a request for treatment providers who perform knee surgery on 55-year old males living in Los Angeles may be received in step 1505. The blockchain may be queried for effectiveness scores for treatment providers that meet these criteria in step 1510. Then the treatment providers associated with the received effectiveness scores may be sorted by one or more criteria (e.g., highest effectiveness score, shortest distance from an address, etc.) in step 1520 and these results may be provided to the patient in step 1525.

Because it is difficult to alter information stored on a blockchain, determinations made therefrom are more reliable than determinations made using data stored in other locations. As a result, the wellness, improvement, and effectiveness scores determined by the processed described herein are made using data that is difficult to corrupt or otherwise tamper with. This results in a high level of confidence in the accuracy of the determinations not offered by more traditional data storage systems and methods. Thus, a patient seeking a recommendation for a treatment, treatment provider, and/or treatment facility determined by the methods disclosed herein may more trustworthy and therefore, more valuable to the patient.

We claim:

1. A computer-implemented method comprising:
   in response to verification of an electronic key transmitted by a patient device, transmitting, by a first server, an outcome measurement device (OMD) electronically to the patient device for display on a display screen of the patient device, the first server communicatively coupled to an array of computers and the patient device, the array of computers configured to store a blockchain including one or more data blocks with associated payloads and information relating to corresponding payloads, the payloads including information relating to corresponding patients, the array of computers coupled to a second server that is in turn coupled to one or more databases configured to store patient information including the OMD, the patient information identified in the databases by a link stored as at least one data block of the one or more data blocks of the blockchain;
   electronically generating a smart contract, by the first server, and adding the smart contract to the OMD, the smart contract including one or more auto-executing routines initiated upon satisfaction of one or more requirements including a requirement that a patient associated with the patient device execute a medical questionnaire of the OMD via the patient device and that a condition be fulfilled responsively to a determination that the requirement has been met, wherein execution of the smart contract through the patient device provides a privilege enabling the patient to schedule a treatment through a treatment facility device in communication with the second server with a treatment;
   in response to receiving a set of responses to the medical questionnaire from the patient device, storing the set of responses to the medical questionnaire, by the second server, through the link;
   determining, by the first server, that the medical questionnaire has been completed and that the requirement has been met; and
   in response to fulfillment of the condition, communicating, by the first server, an indication of the privilege that enables the patient to schedule the treatment with the treatment provider responsively to a determination that the requirement has been met to the patient device.

2. The computer-implemented method of claim 1, further comprising:
   digitally signing, by the first server, the set of responses prior to generating another payload including the set of responses, wherein the another payload further includes a digital signature indicative of the digital signing of the set of responses and a payload hash associated with the another payload includes a hash of the set of responses and the digital signature.

3. The computer-implemented method of claim 2, further comprising:
   using a patient identifier to identify the patient;
   receiving, by the first server, the patient identifier prior to generating the another payload including the set of responses, wherein the another payload further includes the patient identifier and the payload hash includes a hash of the set of responses and the patient identifier.

4. The computer-implemented method of claim 2, wherein the payload further includes a patient key and the payload hash includes a hash of the patient key.

5. The computer-implemented method of claim 1, further comprising:
   packaging, by the first server, the set of responses into a second data block configured for storage on the blockchain, wherein the packaging comprises:
   generating a hash of a data block stored previously to the second block on the blockchain;
   generating a second payload that includes the set of responses;
   generating a payload hash that includes a hash of the second payload; and
   broadcasting, by the first server, the second data block to the blockchain.

6. The computer-implemented method of claim 5, wherein the medical questionnaire is associated with a scoring procedure for scoring the set of responses, the method further comprising:
   determining, by the first server, a wellness score for the patient by applying the scoring procedure to the set of responses; and
   packaging, by the first server, the wellness score for storage on the blockchain; and
   broadcasting, by the first server, the wellness score to the blockchain.

7. The computer-implemented method of claim 5, further comprising:
adding, by the first server, an indication of fulfillment of the condition to a next payload for a subsequently-packaged data block configured for storage on the blockchain.

8. The computer-implemented method of claim 5, wherein the medical questionnaire is a first medical questionnaire and the set of responses is a first set of responses, the method further comprising:
communicating, by the first server, a second medical questionnaire to the patient device for display on the patient device;
receiving, by the first server, a second set of responses to the second medical questionnaire from the patient device, the second set of responses being entered into the patient device;
packaging, by the first server, the second set of responses into a second data block configured for storage on the blockchain, the packaging comprising:
generating a second hash of a second data block previously stored on the blockchain;
generating a second payload that includes the second set of responses;
generating a second payload hash that includes a hash of the second payload; and
broadcasting, by the first server, the second data block to the blockchain.

9. The computer-implemented method of claim 8, further comprising:
querying, by the first server, the blockchain for the first and second set of responses;
receiving, by the first server, the first and second set of responses from the blockchain responsively to the query;
determining, by the first server, an improvement score for the patient by comparing the first and second set of responses, the improvement score indicating a result of the comparison.

10. The computer-implemented method of claim 5, wherein the blockchain is a private blockchain and data blocks stored on the private blockchain are required to be configured according to one or more parameters required for storage of the data blocks on the private blockchain, further wherein packaging the data blocks for storage on the private blockchain includes generation of the data blocks in compliance with the one or more parameters.

11. The computer-implemented method of claim 5, wherein the blockchain is a public blockchain and the data blocks stored on the public blockchain are required to be configured according to one or more parameters required for storage of the data blocks on the public blockchain, further wherein packaging the data blocks for storage on the public blockchain includes generation of the data blocks in compliance with the one or more parameters.

12. The computer-implemented method of claim 1, wherein the condition includes automatic communication of a message to a device of the treatment provider, the method further comprising:
automatically communicating, by the first server, the message to the device of the treatment provider responsively to a determination, by the first server, that the requirement has been met.

13. The computer-implemented method of claim 1, wherein the condition includes automatic communication of a message that includes a billing code for the treatment to a treatment facility device of a medical insurance company associated with the patient, the method further comprising:
automatically communicating, by the first server, the message that includes the billing code for the treatment to the treatment facility device of the medical insurance company responsively to a determination, by the first server, that the requirement has been met.

14. The computer-implemented of claim 1, further including formatting the OMD and the smart contract for storage on the blockchain.

15. The computer-implemented of claim 1, further including broadcasting the OMD and the smart contract on the blockchain.

16. The computer-implemented method of claim 1, further including responding, by the first server, to a request for the OMD from the patient device, wherein the request is automatically generated when the patient logs onto a patient account associated with the patient.

17. The computer-implemented of claim 1, further including causing displaying, through an interface of the first server:
a tally of tokens earned by a provider of patients, including the patient, for sending OMDs to the patients to follow up after patient office visits and sending out OMDs according to a timeline or schedule,
a message indicating information on one or more incentives for sending the OMDs, by the provider, to the patients, wherein the one or more incentives must be earned to reach a reward.

18. The computer-implemented of claim 17, further including providing through a provider portal a number of tokens earned based on:
use of the provider portal,
updates of information stored via the provider portal,
updates to patient accounts,
interactions with the patients,
initiating communication of the OMD to the patient, and
review of responses to the OMD.

* * * * *